United States Patent
Cau et al.

(10) Patent No.: US 12,402,961 B2
(45) Date of Patent: Sep. 2, 2025

(54) SURGICAL ROBOTIC SYSTEM COMPRISING SPHERICAL WRIST

(71) Applicant: MICROSURE B.V., Son (NL)

(72) Inventors: Raimondo Cau, Son (NL); Cornelis Van Giessen, Son (NL)

(73) Assignee: MICROSURE B.V., Son (NL)

( * ) Notice: Subject to any disclaimer, the term of this patent is extended or adjusted under 35 U.S.C. 154(b) by 423 days.

(21) Appl. No.: 17/996,432

(22) PCT Filed: Apr. 13, 2021

(86) PCT No.: PCT/EP2021/059598
§ 371 (c)(1),
(2) Date: Oct. 17, 2022

(87) PCT Pub. No.: WO2021/213851
PCT Pub. Date: Oct. 28, 2021

(65) Prior Publication Data
US 2023/0233273 A1    Jul. 27, 2023

(30) Foreign Application Priority Data

Apr. 23, 2020   (EP) .................................... 20171161

(51) Int. Cl.
*A61B 34/00* (2016.01)
*A61B 17/29* (2006.01)
*A61B 34/30* (2016.01)

(52) U.S. Cl.
CPC .............. *A61B 34/30* (2016.02); *A61B 17/29* (2013.01); *A61B 34/71* (2016.02); *A61B 2034/305* (2016.02)

(58) Field of Classification Search
CPC ......... A61B 34/30; A61B 17/29; A61B 34/71; A61B 2034/305; A61B 18/1445; A61B 34/35; A61B 34/37
See application file for complete search history.

(56) References Cited

U.S. PATENT DOCUMENTS

| | | | |
|---|---|---|---|
| 4,989,795 A | * | 2/1991 | de Lackner ........... B02C 15/004 241/117 |
| 2004/0049205 A1 | * | 3/2004 | Lee ........................ A61B 34/37 606/130 |

(Continued)

FOREIGN PATENT DOCUMENTS

| | | |
|---|---|---|
| WO | 2014055979 A1 | 4/2014 |
| WO | 2015061756 A1 | 4/2015 |
| WO | WO-2019228169 A1 * 12/2019 | ....... A61B 17/00234 |

OTHER PUBLICATIONS

European Patent Office, Office Action Issued in Application No. 20171161.1 Nov. 6, 2024, Netherlands, 6 pages.

(Continued)

*Primary Examiner* — Benjamin J Klein
*Assistant Examiner* — Alisha J Sircar
(74) *Attorney, Agent, or Firm* — McCoy Russell LLP

(57) ABSTRACT

A surgical robotic system is provided comprising a wrist comprising a surgical instrument and an elongated shaft configured to transmit actuation forces from a drive assembly to the spherical wrist to actuate rotation of the spherical wrist. The surgical instrument is a hinged surgical instrument comprising jaws, wherein the jaws are biased in a normally open position by a resilient biasing element, wherein the surgical instrument is actuatable by the drive assembly towards a closed position by a preloaded string which runs from the drive assembly through the elongated shaft to the surgical instrument and which preloads the surgical instrument.

12 Claims, 16 Drawing Sheets

(56) References Cited

U.S. PATENT DOCUMENTS

| | | | |
|---|---|---|---|
| 2008/0119870 A1* | 5/2008 | Williams | A61B 34/71 606/130 |
| 2013/0066332 A1* | 3/2013 | Sutherland | A61B 34/30 606/1 |
| 2014/0035305 A1* | 2/2014 | Ludwig | B25J 1/04 294/200 |
| 2014/0243887 A1 | 8/2014 | Kim et al. | |
| 2015/0119638 A1* | 4/2015 | Yu | A61B 1/0057 600/102 |
| 2017/0021508 A1* | 1/2017 | Marshall | B25J 9/102 |
| 2017/0035526 A1* | 2/2017 | Farritor | A61B 1/00137 |
| 2017/0143436 A1* | 5/2017 | Lathrop | A61B 34/30 |
| 2017/0252096 A1* | 9/2017 | Felder | A61B 18/1445 |
| 2019/0216552 A1* | 7/2019 | Palmowski | B25J 9/126 |
| 2020/0038121 A1* | 2/2020 | Yang | A61B 90/06 |
| 2020/0093553 A1* | 3/2020 | Nelson | A61B 34/71 |
| 2021/0220063 A1* | 7/2021 | Kapadia | A61B 34/30 |

OTHER PUBLICATIONS

ISA European Patent Office, International Search Report and Written Opinion Issued in Application No. PCT/EP2021/059598, Jul. 7, 2021, WIPO, 12 pages.

\* cited by examiner

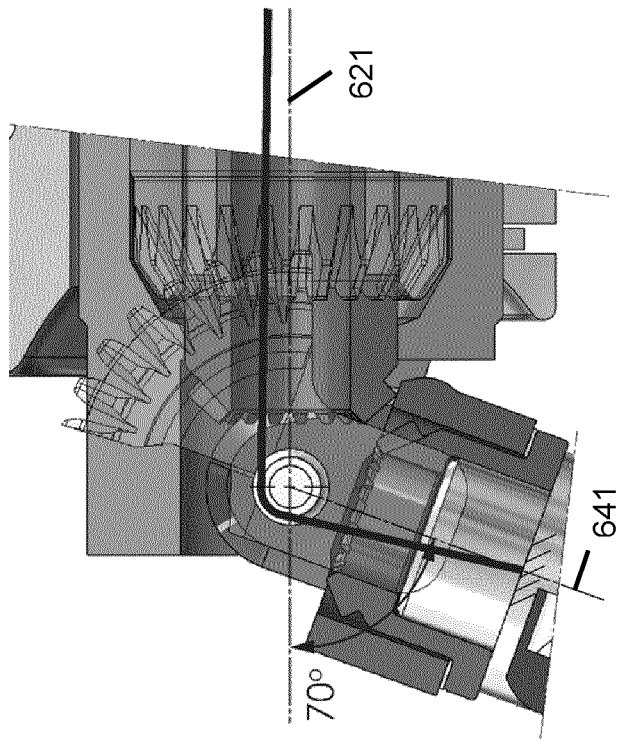
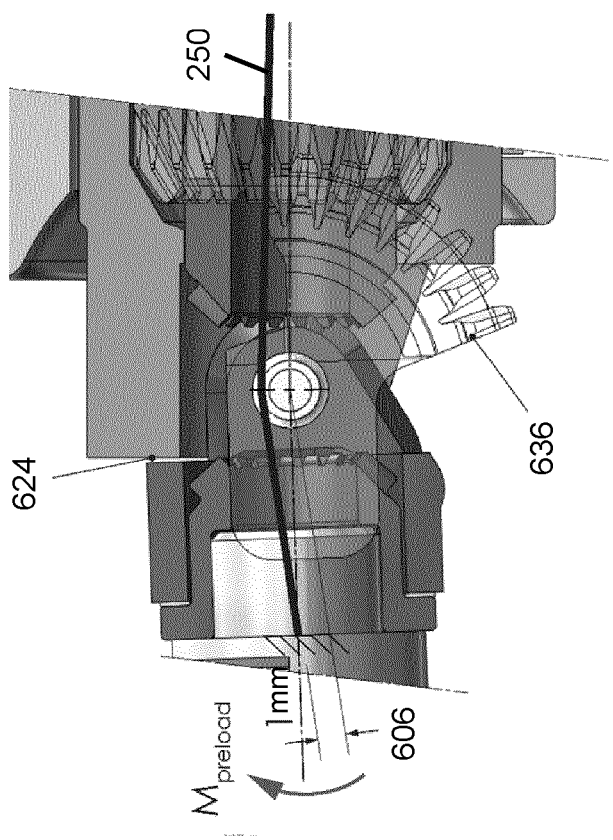
Fig. 11B
Fig. 11A

SURGICAL ROBOTIC SYSTEM COMPRISING SPHERICAL WRIST

CROSS REFERENCE TO RELATED APPLICATIONS

The present application is a U.S. National Phase of International Application No. PCT/EP2021/059598 entitled "SURGICAL ROBOTIC SYSTEM COMPRISING SPHERICAL WRIST," and filed on Apr. 13, 2021. International Application No. PCT/EP2021/059598 claims priority to European Patent Application No. 20171161.1 filed on Apr. 23, 2020. The entire contents of each of the above-listed applications are hereby incorporated by reference for all purposes.

TECHNICAL FIELD

The invention relates to a surgical robotic system for microsurgery.

BACKGROUND AND SUMMARY

An increasing number of surgeries is performed by means of surgical robots. These surgical robots may comprise so-called manipulators which generally have an end effector which handles a surgical instrument acting upon the patient.

In microsurgical procedures, such instruments include needle holders, forceps, vessel dilators and scissors, while the precision, stability and dexterity of the handling of such instruments are critical aspects in the outcome of the procedure. Various microsurgical robotic platforms are developed to enhance these aspects.

During conventional microsurgery, referring to microsurgery performed with hand-held instruments, the so-called instrument roll, referring to the rotation of the instrument around its longitudinal axis, may be a critical movement to allow controlled passage of a surgical needle into tissue that is to be sutured. The surgical needle is typically curved over an arc of ⅜th of a circle, and is held perpendicularly between the jaws of the instrument. Rolling the instrument may allow the needle to follow its natural curvature while it is passing through the tissue, thereby avoiding applying excessive (detrimental) force on the tissue or needle. Such curvature typically allows passing the needle through multiple parts of tissue in one fluent rotational movement.

In surgical robotic systems, a roll movement may sometimes be achieved by having the surgical manipulator as a whole execute a combination of other degrees of freedom. However, this may feel counterintuitive to the user and may have a negative effect on the precision and stability of the tip of the instrument, since each actuated degree of freedom inherently is a source of tracking error during movement.

WO2014/055979A1 describes an articulating device which may be articulated and/or translated about five axes, as also shown in FIGS. 13A-14F. This may include a roll movement about the longitudinal axis of a tissue grasping device.

A disadvantage of WO2014/055979A1 may be that the tissue grasping device held by the articulating device may not be actuated with sufficiency accuracy.

An object of the invention is to obtain a surgical robotic system which comprises a spherical wrist comprising a surgical instrument and which allows the surgical instrument to be actuated with improved accuracy.

An Aspect of the Invention Provides a Surgical Robotic System, Comprising:

a spherical wrist comprising a surgical instrument, wherein the spherical wrist comprises a yaw axis, a pitch axis and a roll axis to provide the surgical instrument with three rotational degrees of freedom, the three rotational degrees of freedom including a roll rotation about a longitudinal axis of the surgical instrument;

an elongated shaft, wherein the spherical wrist is attached to a distal end of the elongated shaft, wherein a drive assembly is attached to a proximate end of the elongated shaft, wherein the elongated shaft is configured to transmit actuation forces from the drive assembly to the spherical wrist to actuate rotation of the spherical wrist;

wherein the surgical instrument is a hinged surgical instrument comprising jaws, wherein the jaws are biased in a normally open position by a resilient biasing element, wherein the surgical instrument is actuatable by the drive assembly towards a closed position by a string which runs from the drive assembly through the elongated shaft and the spherical wrist to the surgical instrument, and wherein the string is preloaded to preload the surgical instrument and the spherical wrist.

The above measures involve a surgical robotic system, which may be a so-called master-slave system, which may comprise a manipulator holding a surgical instrument. The manipulator may comprise a spherical wrist arranged at a distal end of an elongated shaft. Here, the term 'distal' may refer to an end which is facing the patient and away from a base structure of the surgical robotic system. The surgical instrument may be held by the spherical wrist, and may be removable, for example to exchange and/or separately sterilize the surgical instrument. The spherical wrist may comprise at least three axes of rotation, namely a yaw axis, a pitch axis and a roll axis. The wrist may be spherical in that the three axes of rotation may jointly intersect each other. Thereby, the spherical wrist may provide the surgical instrument with at least three rotational degrees of freedom (DOF), enabling the surgical instrument to be suitably oriented in a surgical workspace. The roll axis of the spherical wrist may be aligned with a longitudinal axis of the surgical instrument. Thereby, the surgical instrument may perform a roll movement around the chosen longitudinal axis of the surgical instrument, which may allow controlled passage of a surgical needle, which may be held by the surgical instrument during surgery, into tissue that is to be sutured.

Attached to the proximate end of the elongated shaft may be a drive assembly, which may generate actuation forces and which may be transmitted by the elongated shaft to the spherical wrist to actuate any rotation of the spherical wrist. Here, the term 'proximate' may refer to an end which is facing away from the patient and towards a base structure of the surgical robotic system. To generate the actuation forces, the drive assembly, which may also be referred to as 'drive-box' or 'actuation mechanism' elsewhere, may comprise one or more electric motors or other type of actuators. The elongated shaft may thus function as a slender supporting structure for the spherical wrist, e.g., to enable the spherical wrist and its surgical instrument to be positioned close to the patient without unnecessarily obstructing the workspace. In addition, the elongated shaft may function as a transmission mechanism for the actuation forces generated by the drive assembly. Thereby, it may not be needed for the spherical wrist itself to comprise all required actuators, such as electric motors. This may reduce the size and weight of the spherical wrist, which in turn may improve the handling and controllability of the instrument and reduce cluttering at the operation site.

The surgical instruments may be a hinged surgical instrument comprising jaws. Hinged surgical instruments are known per se, and may include different types of hinged surgical instruments, e.g., with different lengths, means of manipulation, hinging points or mechanisms. In general, such hinged surgical instruments may comprise two jaws, which may by themselves also be referred to as 'beaks' or 'arms' and as a pair form a grasper, cutter, dilator or coagulator, with the surgical tool being typically hinged at the front or at the rear end of the instrument. The surgical instrument held by the surgical robotic system may be a normally-open type of surgical instrument, which may mean that in a passive, e.g., non-actuated state, the surgical instrument's jaws may be open or even fully opened, while in an actuated state, the surgical instrument's jaws may be closed. It is known to establish such a normally-open passive state in various ways, which in general may involve a resilient biasing element, such as a spring or an elastic hinge or a nitinol element, which may bias the jaws into the open position when no or only insufficient actuation force is applied to the surgical instrument.

The surgical instrument may be actuated towards the closed position by the drive assembly. In accordance with the above measures, this may be established by a string which may run from the drive assembly via the elongated shaft to the surgical instrument. For example, the drive assembly may 'pull' the string to effect a closing of the surgical instrument. The string may be preloaded, which may mean that the string may be tensioned such that a preload force is exerted on the surgical instrument even in the passive state. However, the preload force may be chosen such that it may not fully compensate for the opening force exerted by the resilient biasing element. The preload force may therefore in itself not cause actuation of the surgical instrument. In other words, the force exerted on the jaws by the resilient biasing element may be larger than the string preload force. As the tension force in the string is increased by the drive assembly, the total string force, which may equal a constant preload force and a variable actuation force, may become larger than the force of the resilient biasing element, thus resulting in a closing movement of the jaws. This may be achieved during design or setup of the surgical robotic system by suitably selecting or configuring the resilient biasing element so that the passive jaw opening force has a suitable value in relation to the preload force, and/or by suitably tensioning the preload string such that its preload force has a suitable value in relation to the preload force. Thereby, the surgical instrument may remain normally-open in the passive state.

Compared to WO2014055979, where the actuation of the jaws of the tissue grasping device may be provided by a concentric tube-gear mechanism, the above measures use a string for actuation which also serves as a preloading element for at least the actuation of the surgical instrument. Thereby, the constant (baseline) preload force may add up to the actuation force on the jaws when the surgical instrument is actuated, or specifically, when the instrument's jaws are closed. This may remove or at least significantly reduce play in the actuation of the surgical instrument while increasing the stiffness of the surgical instrument and thereby improving their positioning accuracy when needed, e.g., while the instrument is holding and manipulating a needle. The string may also preload the transmission mechanism contained in the elongated shaft, which may also remove or at least significantly reduce play in the actuation of the spherical wrist, in addition to reducing the play in the actuation of the surgical instrument. Effectively, the preload string may reduce play in the overall kinematic structure by which the surgical instrument is positioned and actuated. Conversely, when the actuation force and thus tension on the jaws is released, the total force exerted by the string on the overall kinematic structure may be diminished since only the constant (baseline) preload force may remain, thereby reducing friction (resistance) in the mechanisms and allowing faster movements. Furthermore, also in the passive state of the surgical instrument, e.g., when the jaws are opened, the preload force may remove or at least significantly reduce play in the overall kinematic structure so as to establish a certain baseline precision.

WO2014055979 lacks such a preloading element, meaning that there is a certain amount of play in the tube-gear mechanism, which is detrimental to the positioning accuracy of the instrument. Accordingly, compared to WO2014055979, an improved positioning accuracy may be obtained.

Optionally, the elongated shaft is a tube assembly comprising a concentric arrangement of at least three tubes, wherein each respective tube is configured to transmit a respective actuation force from the drive assembly to the spherical wrist to effect a rotation about a respective axis, wherein said preloading of the string applies an axial tension on the tube assembly. To transmit the actuation forces generated by the drive assembly, the elongated shaft may comprise a concentric arrangement of tubes, in which a respective tube may, by its rotation about its longitudinal axis, transmit an actuation force to the spherical wrist to effect a rotation about a respective axis of rotation. Effectively, each tube may function as a driveshaft for a respective rotational DOF. Such a concentric arrangement of tubes may be an advantageous transmission mechanism, but which may also exhibit a certain amount of play. Since the string runs through the tube assembly to the surgical instrument, the preloading of the string may also cause an axial tension to be applied to the tube assembly, which in turn may remove or at least significantly reduce play in the tube assembly. This may result in improved measurability and, consequently, positioning accuracy when actuating any rotation of the spherical wrist. As such, the rotational positioning of the surgical instrument may be carried out more accurately.

Optionally, the string is elastically attached to or in the surgical instrument via a resilient fixation element. For example, the resilient fixation element may be a pulley, and the string may be attached to the pulley by being wound multiple revolutions around the pulley. Other examples of resilient fixation elements include but are not limited to a lever mechanism, a screw mechanism, a gear mechanism, a rack-and-pinion mechanism, a spindle mechanism, etc., with each mechanism being configured to exert tension on the string Optionally, the string is elastically attached to or in the drive assembly via a resilient fixation element. The resilient fixation element at the drive assembly side may be of a type as described for the surgical instrument.

Optionally, the string comprises or is made out of ultra-high-molecular-weight polyethylene, UHMWPE, or high-modulus polyethylene, HMPE, fibers. For example, the string may be made out of Dyneema fibers. Any of such types of fibers may be as strong as steel, easily bend over small radii, have a low friction coefficient with respect to itself and other materials, and may be hard to cut. Moreover, such types of fibers may have a relative low cost, which allows the string to be disposable, which may be advantageous with respect to the sterile requirements of a surgical workspace.

Optionally, the spherical wrist is actuatable by the tube assembly to rotate about the roll axis via a roll bevel gear and about the pitch axis via a pitch bevel gear.

Optionally, the string runs over a pitch bevel gear so as to apply a lateral force on said shaft to preload the pitch bevel gear onto the yaw and roll bevel gears. This may further reduce play in the actuation of the rotations of the spherical wrist, and in particular, in the actuation of the pitch rotational DOF.

Optionally, the spherical wrist is directly actuatable by the tube assembly to rotate about the yaw axis via a respective tube of the tube assembly.

Optionally, the yaw axis, the pitch axis and the roll axis of the spherical wrist form a serial kinematic chain, wherein the roll axis is placed last in the serial kinematic chain. By placing the roll axis last in the serial kinematic chain, it may be ensured that the spherical wrist may always be rotated about its roll axis without influencing the yaw and pitch axis, which in turn may mean that the surgical instrument may always be rotated about the chosen longitudinal axis while the other rotational degrees of freedom remain static. This may be advantageous given the importance of the roll movement in microsurgery.

Optionally, the at least three tubes of the tube assembly are swaged at the distal end of the tube assembly. As is known per se, swaging is a (cold) forming process for reducing a tube diameter, which may be applied locally. By swaging the distal end of the tube assembly, which is connected to the wrist, larger diameter tubes may be used to transmit torque to the wrist, instead of using smaller straight tubes with a direct fit to the wrist. As a result, the stiffness of the tubes may be increased with respect to a design with non-swaged tubes, and virtual backlash may be decreased.

Optionally, the tube assembly is coupled to the drive assembly and/or to the spherical wrist with a respective coupling part, wherein the respective coupling part comprises a lipid- or greased-filled axial labyrinth seal for sealing between the respective tubes. The lipid- or grease-filled axial labyrinth seals may create a sterile barrier, which may for example prevent non-sterile contamination by the drive assembly during surgery. The use of such seals may in general allow a coupling between sterile components and non-sterile components, without contaminating the sterile zone.

Optionally, the hinged surgical instrument comprises a stationary jaw and a clamping jaw, wherein the clamping jaw is actuatable by the string. Instead of using a symmetrically actuated surgical instrument, one of the jaws of the surgical instrument may be held stationary while the other jaw is actuated by the string. Such an asymmetric design may reduce the number of components, provide a stationary reference point, and/or may provide more space for an actuation mechanism.

Optionally, the roll axis of the spherical wrist is aligned with a longitudinal axis of the stationary jaw of the surgical instrument. By having the roll axis of the spherical wrist aligned with the longitudinal axis of the stationary jaw, instead of for example with a longitudinal symmetry axis of the surgical instrument, the roll axis may be aligned with a stationary reference point. For example, a surgeon may use the tip of the stationary jaw as a reference point when initiating a roll movement, in the knowledge that the tip of the stationary jaw will remain (at least substantially) at its present position. This may enable the surgeon to more easily and accurately position the surgical instrument in the surgical workspace. In some examples, the jaws may be color marked or otherwise visually distinguished from each other to allow the surgeon to easily distinguish the stationary jaw from the clamping jaw.

Optionally, the surgical instrument comprises a sliding pulley, and wherein the string runs over the sliding pulley to reduce friction influencing the actuation force of the surgical instrument. The sliding pulley may compensate for the lever ratio of the clamping jaw, and may thereby reduce the required actuation force.

Optionally, the surgical instrument comprises at least one of:

a mechanical stop to avoid over-actuation of the surgical instrument, and a mechanical stop to limit opening of the jaws.

It will be appreciated by those skilled in the art that two or more of the above-mentioned embodiments, implementations, aspects and/or optional aspects of the invention may be combined in any way deemed useful.

BRIEF DESCRIPTION OF THE FIGURES

These and other aspects of the invention are apparent from and will be elucidated with reference to the embodiments described hereinafter. In the drawings, FIG. 1 schematically illustrates a manipulator of a surgical robotic system which comprises a strut assembly and a wrist for holding a surgical instrument;

FIG. 5A shows a sideview of a part of the manipulator with respect to the strut drive axis, while

FIG. 10A shows a sideview of the yaw and roll plain bearing with preload elements, while FIG. 10B shows a sectioned view along planes A-A and B-B;

FIG. 11A shows a sectioned side view of the spherical wrist at a pitch angle of 0 degrees, with bevel gears made transparent for visibility;

FIG. 11B shows a sectioned side view of the spherical wrist at a pitch angle of 70 degrees, with bevel gears made transparent for visibility;

It should be noted that items which have the same reference numbers in different figures, have the same structural features and the same functions, or are the same signals. Where the function and/or structure of such an item has been explained, there is no necessity for repeated explanation thereof in the detailed description.

DETAILED DESCRIPTION

Figure 1:
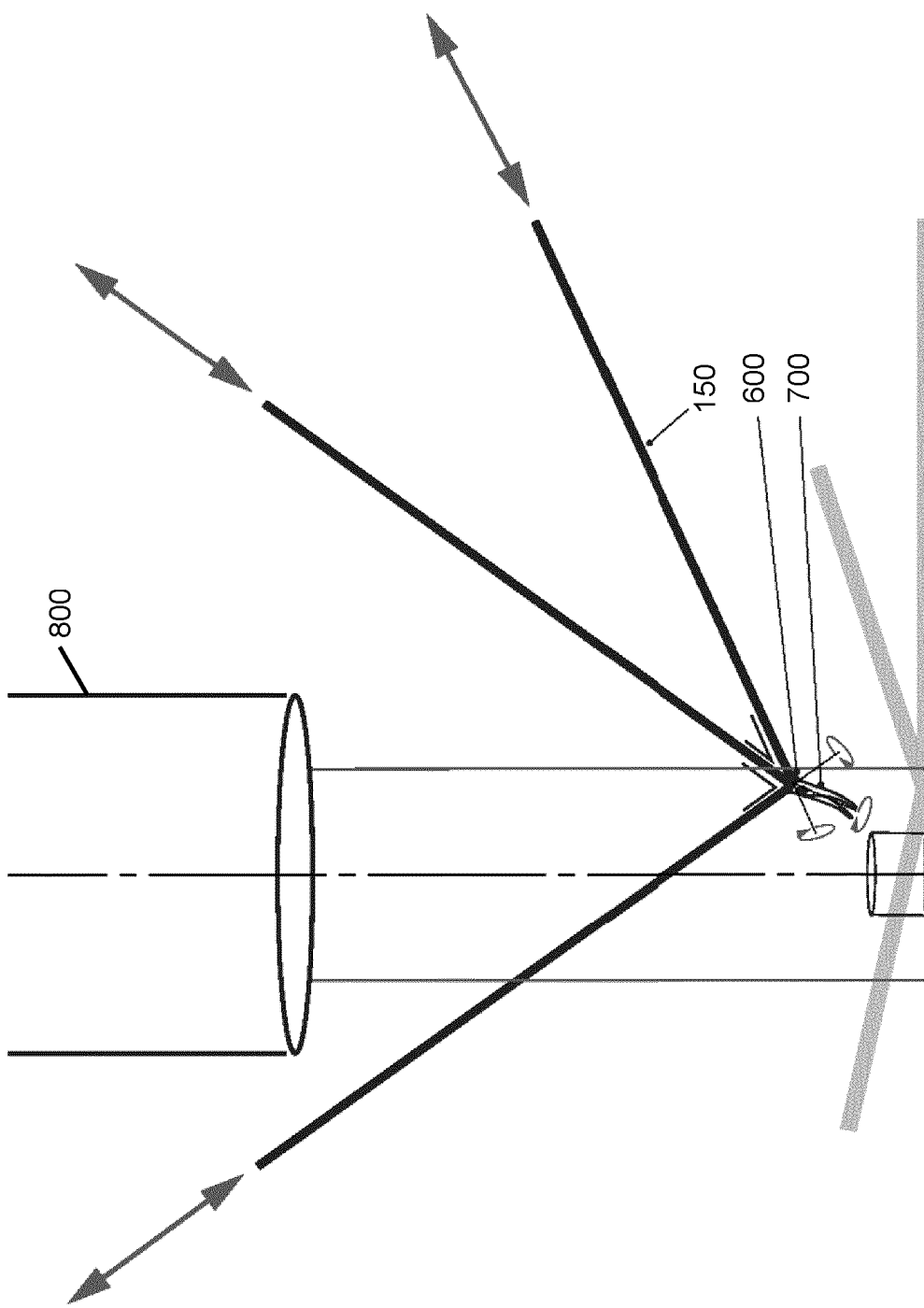

FIG. 1 schematically illustrates a strut assembly of a surgical robotic system. The strut assembly is shown to comprise three struts 150 which are each actuatable in longitudinal direction. Attached to a distal portion of the strut assembly is a wrist 600 for holding a surgical instrument 700, which is also simply referred to as 'instrument'. The wrist 600 may be a spherical wrist as also explained elsewhere in this specification. The strut assembly formed by the struts 150, the wrist and the surgical instrument may together form at least part of a so-called manipulator of the surgical robotic system.

It is noted that FIG. 1 and others show part of the manipulator of the surgical robotic system, while many other parts of the surgical robotic system, such as attachment frames, control subsystems, control devices ('master devices') and the like are not shown. These non-depicted parts of the surgical robotic system may take any suitable forms, including known forms, which are compatible with the manipulator.

The manipulator which is illustrated in FIG. 1 in a highly schematic way may form a hybrid kinematic structure which combines favorable properties of both serial and parallel kinematics structures. As can be seen in FIG. 1, the three struts 150 may provide three translational DOF in a parallel kinematic setup, while the wrist 600 may provide three rotational DOF in a serial kinematic setup. For rotational DOF, a relatively large range of motion may be desired but which may be relative inaccurate. For translational DOF, a relative accurate range of motion may be desired but which may be relatively small. These requirements may be jointly met by using serial kinematics for rotational DOF combined with parallel kinematics for translational DOF.

The hybrid kinematic structure which is conceptually shown in FIG. 1 may provide one or more advantages. For example, such a structure may enable a low mass per DOF and therefore enable efficient use of mass. Another example of an advantage is that in such a structure, relatively few DOF may require strict stiffness constrains due to the aforementioned use of parallel kinematics. The structure of FIG. 1 may also avoid or reduce blocking the view of the microsurgical workspace for either a microscope 800 or the direct view of the (assistant) surgeon. For example, the structure may allow the microscope 800 to fit in between the struts 150 to closely approach the microsurgical workspace. As will also be described elsewhere, the translational DOF may be actuated, measured and supported at a base frame away from the surgical workspace, which may enable the use of off-the-shelf components which may limit cost and may increase performance. In some examples, weight compensation may be employed, for example at the base frame and which may be tilt independent.

Various components of the robotic surgical system which achieve and/or contribute to realizing the above-mentioned advantages are described in the following in more detail. It is noted that such components may also be used independently from each other. For example, the strut assembly as described in the specification may be used with another type of wrist, and/or the spherical wrist as described in this specification may be mounted to another type of assembly to provide the translational DOF, and/or the wrist may be configured to actuate a different type of instrument.

Figure 2:
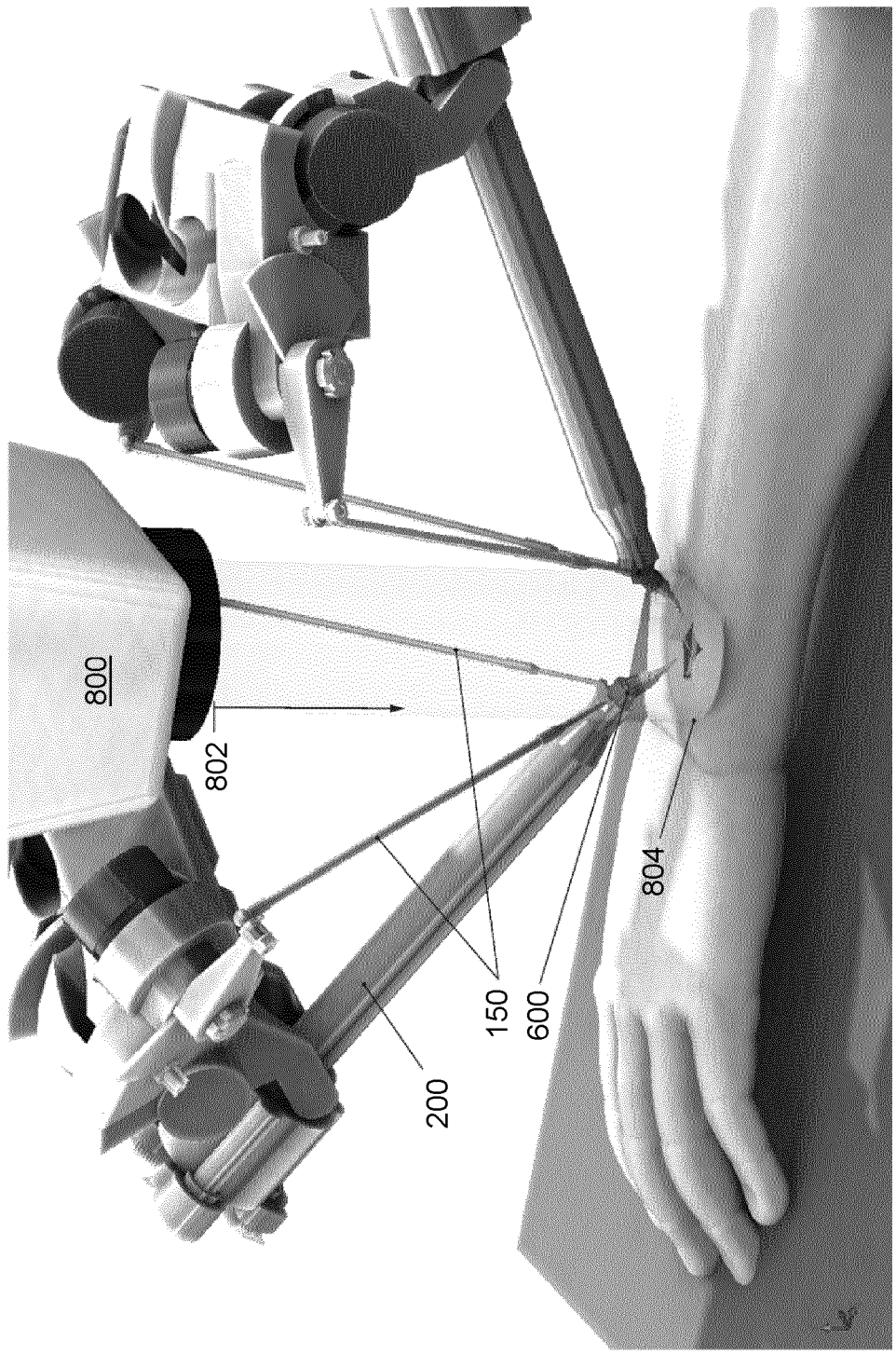
FIG. 2 shows two instances of the manipulator of the surgical robotic system in a setup for use in Lymphogenous Anastomosis (LVA) surgery.

FIG. 2 gives an impression of the surgical robotic system during use, which shows a setup in which two manipulators of the type as shown in FIG. 1 and elsewhere are shown in use during Lymphogenous Anastomosis (LVA) surgery. Each manipulator is shown to comprise a strut assembly formed by two struts 150 and a third strut in the form of a tube assembly 200. Attached to a distal portion of the strut assembly is a wrist 600 for holding a surgical instrument in a microsurgical workspace. A microscope 800 may be placed in-between the manipulators which may allow a close approach to the microsurgical workspace, e.g., at a relatively small distance 802 to the patient.

Figure 3:
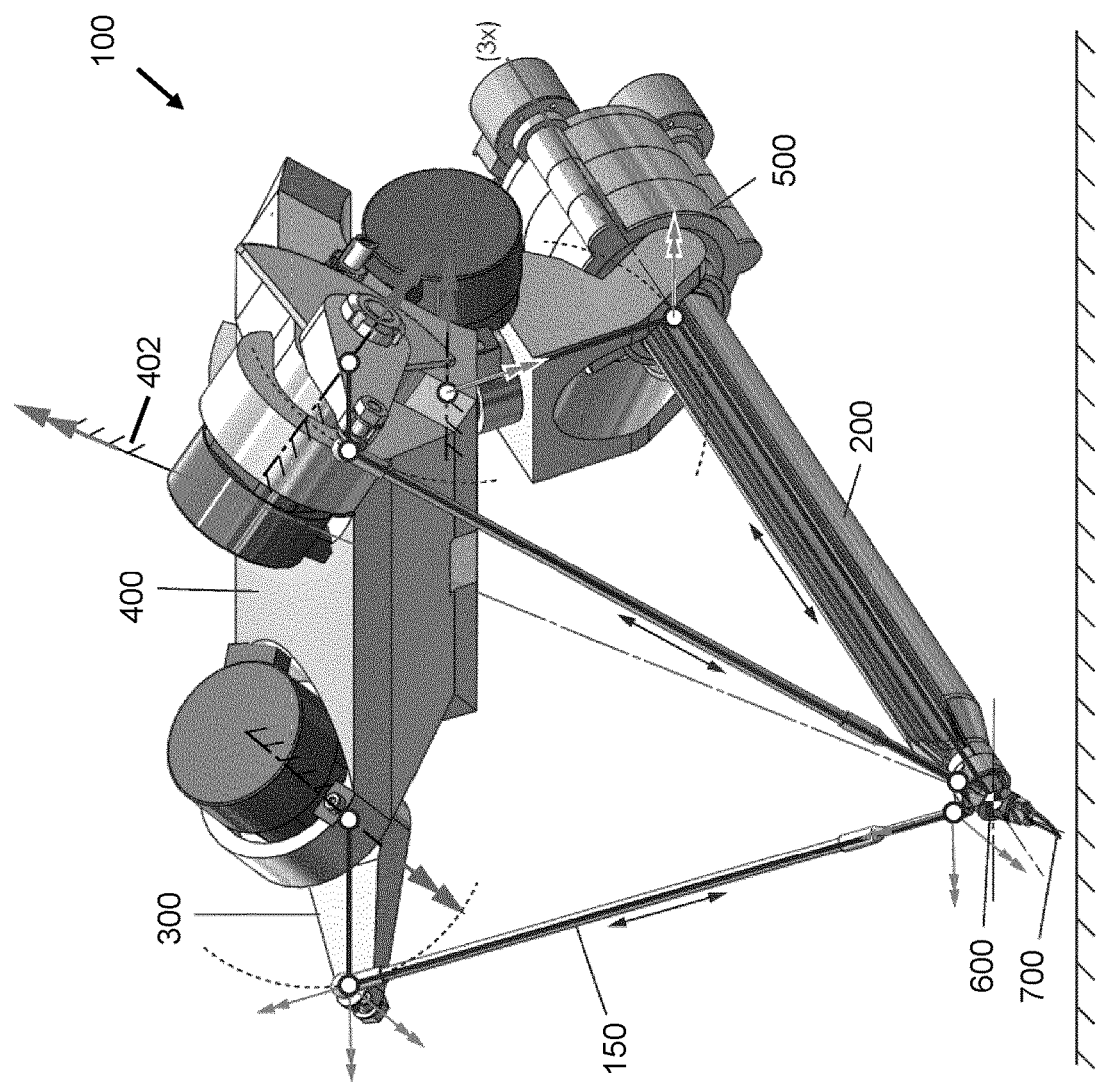
FIG. 3 shows an overview of the manipulator of the surgical robotic system, in which tubes of a tube assembly of the manipulator are partially sectioned.

FIG. 3 shows an overview of the manipulator 100 of the surgical robotic system, in which tubes of a tube assembly 200 of the manipulator are partially sectioned. The manipulator 100 may provide actuation of 7 DOF, namely 3 rotational DOF, 3 translational DOF and an opening/closing of the instrument 700. The rotational DOF may be provided by a spherical wrist 600 near the instrument's tip. As shown in FIG. 3, the translational DOF may be provided via two struts 150 and a tube assembly 200 as a third strut. The wrist 600 may be attached to the distal portion of the tube assembly 200. In other words, the tube assembly 200 may hold the wrist 600.

The neutral lines of the struts 150 and tube assembly 200 may intersect in the wrist's center of rotation. The spherical wrist may be driven by a drive-box 500 via tubes, with the drive-box 500 being arranged on the proximate side of the tube assembly 200. The drive-box 500 may further contain one or more sensors which may measure (directly or indirectly, via a transmission) rotations of the spherical wrist and opening/closing of the surgical instrument. The opening and closing of the instrument 700 may be actuated by the drive-box via a string through the tubes of the tube assembly 200. The struts 150 and tube assembly 200 may be constrained and driven by cranks 300. The struts 150 may be constrained to be axially loaded. The tube assembly 200 may be constrained to be loaded both axially as well as in torsion along its centerline. The cranks 300 may be supported, actuated and measured at a frame 400 which may form a base structure of the manipulator. The frame 400 may be connected to a (further) support structure, which is not shown in FIG. 3 but which may take any suitable form. The support structure is indicated symbolically in FIG. 3 and may allow for a rotation around its indicated axis (reference numeral 402). The rotational axis 402 may intersect with the neutral position of the wrist's center of rotation and may allow the rotation to be locked during operation. This may allow the manipulator to be adjusted in the desired orientation to tilt along with the surgical workspace. Since reorientation may change the orientation of the manipulator with respect to the direction of gravity, gravity may be compensated for, as also described under the heading 'weight compensation'.

Kinematic Setup

As described with reference to FIG. 1, the manipulator 100 may have a hybrid kinematic setup. As seen in FIG. 3, translations may be provided by three parallel branches (struts 150 and tube assembly 200 driven by cranks 300) forming closed kinematic chains, while a spherical wrist 600 may have a serial kinematic structure, as also described under the heading 'spherical wrist layout'. In a specific example of the manipulator 100, the angle between the parallel branches may be 600 in neutral position. This angle may be chosen over an orthogonal setup for increased visibility on and of the workspace, while volume occupancy may be reduced to avoid collisions with the patient, assistant surgeon or the other slave device. In general, the angle may lie between 800-400 or 700-500 or 650-550 in neutral position.

Figure 4:
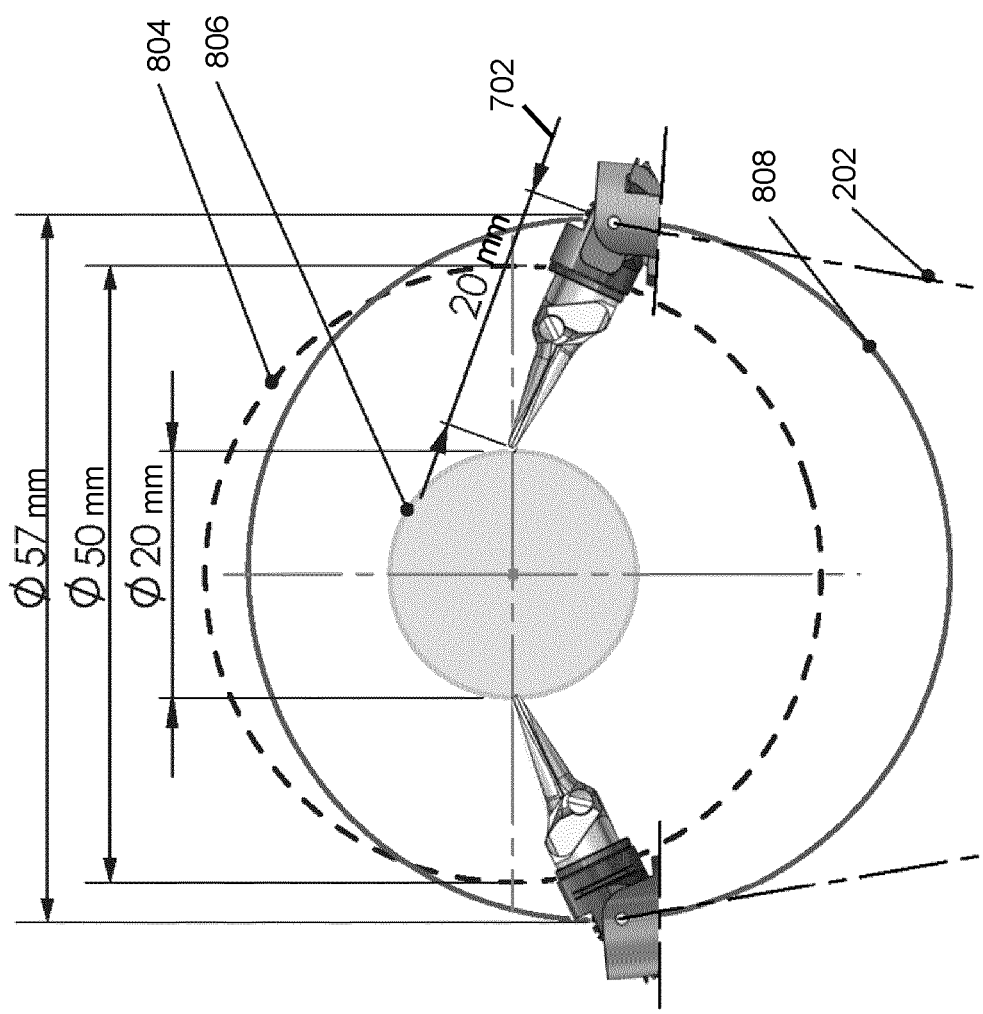
FIG. 4 shows a top-view of a workspace of the surgical robotic system, while further illustrating a desired range of motion for translation.

FIG. 4 shows a top-view of a workspace 806 of the surgical robotic system, the field of view 804 of a microscope, and a desired range of translation 808, which may in the following also be referred to as 'translational stroke'. FIG. 4 may relate to the following: joint angles and link lengths may not need to be optimized for a particular motion trajectory, since motion trajectories may rather be determined by a surgeon during surgery. As such, joint angles and link lengths may be chosen to provide a certain range of motion. This range of motion may for example be determined by summing a minimal translational range of motion and a parasitic translation by the spherical wrist due to rotations, as illustrated in FIG. 4. In the specific example of FIG. 4, this may for example result in a desired translational stroke 808 of approximately 60 mm (57 mm) for a surgical instrument having a length 702 of 20 mm. This translational stroke may be considered as the desired stroke for each of the struts (including the tube assembly), as the range of motion may be approximated by the stroke of its individual links. Even though motions of the struts may be kinematically coupled, by which their motions may be imposed on each other, the performance of the individual links may still mainly determine the performance of the overall strut assembly. Therefore, struts and tube assembly may be treated as being uncoupled during the design stage. Alternatively, kinematic dependencies may be determined and controlled by forward and inverse kinematic modeling to determine the ranges of motion more accurately.

Strut

Figure 5B:
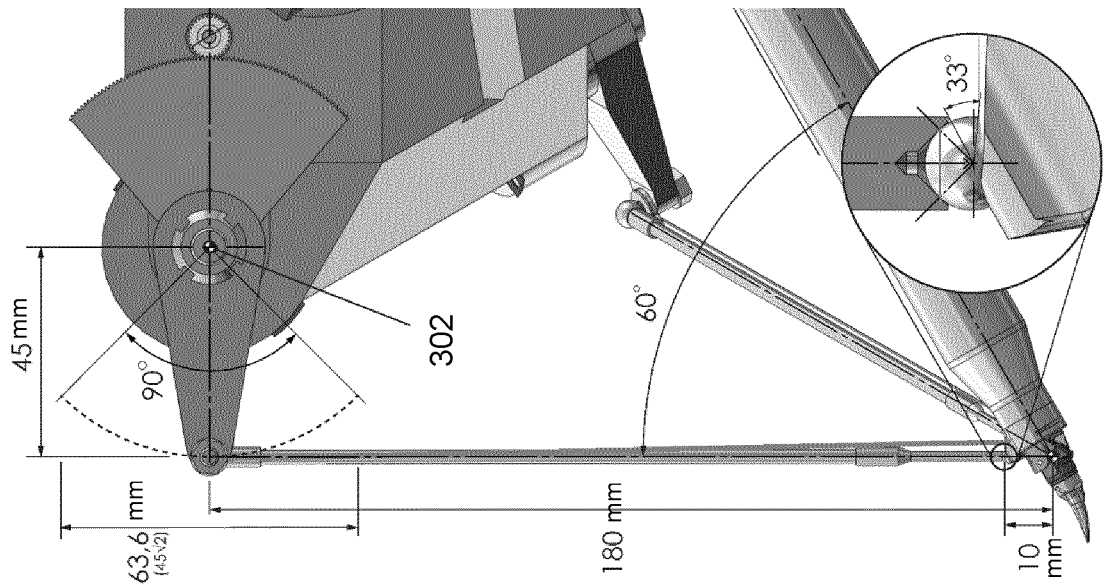
FIG. 5B shows a normal view with respect to the strut drive axis.
Figure 5A:
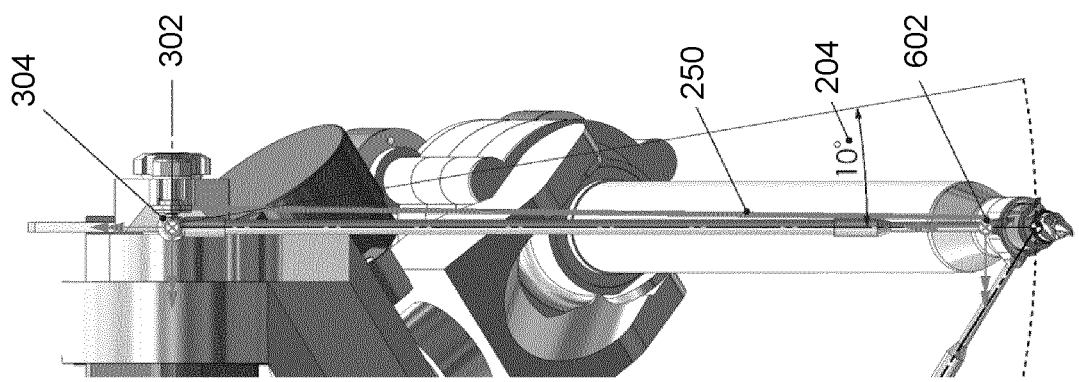

FIG. 5A shows a sideview of a part of the manipulator with respect to the strut drive axis, while FIG. 5B shows a normal view with respect to the strut drive axis. A single strut may constrain 1 DOF, since it may be stiff in axial direction while being compliant in lateral direction. Although lateral translations may be facilitated by elastic deformation of the strut, this may not be preferred since the motion range is too limited and the axial stiffness may be impaired due to off-axis loading. Therefore, ball-joints or similar elements may be used on both sides of the strut, which may facilitate the required angular motions while avoiding impairment of the axial stiffness. It will be appreciated, however, that instead of ball-joints, also other flexible elements may be used, such as flexible hinges. With continued reference to the example of using ball-joints and to FIGS. 5A and 5B, a ball-joint 304 and the crank 300 may be arranged such that they provide the required angular motion through rotation about the axis 302. The largest motion is indicated in the Figures and provided by a ball-joint similar to DIN 71802. Additionally, a conical ball-joint may be chosen for the opposing side, since such a ball-joint may have minimal impact on the view and has a line-contact which may create a stiff connection. In a specific example, a preload of ≈7N may be applied by a spring to engage the conical ball-joint and to avoid backlash in both ball-joints.

Dimensions of the strut, crank and the angular stroke may be chosen to comply with the required range of motion and possible ball-joint angles. FIGS. 5A and 5B show examples of such dimensions and angles (while also showing the tube assembly containing a preload string 250 and a ball-joint 602 in the spherical wrist).

The struts and ball-joints may be part of the sterilized component set, e.g., belonging to those components of the surgical robotic system which are sterilized between uses, since draping of these components may otherwise require a drape in the form of a tent, which may block the view and act as a sail, thereby introducing disturbances during movements. Therefore, in some examples, the struts and ball-joint components may be produced from stainless steel. The strut may be selected to be strain hardened austenitic stainless steel. Such type of steel may obtain a yield stress of ≥1200 MPa, which may reduce risk of component failure. Risk for failure is regarded most likely during sterilization. Equation (1) and (2) indicate the expected maximum buckling and bending force required for a 3 mm strut thickness.

$$F_{buckling} = \frac{\pi^2 E \cdot I}{L^2} = 241\text{N} \quad (1)$$

$$F_{bending} = \frac{8 \cdot \sigma_{0.2} \cdot I}{L \cdot d} = 71\text{N} \quad (2)$$

$$c_{axial} = \frac{EA}{L} = 7854\frac{\text{N}}{\text{mm}} \quad (3)$$

where E is elastic module, L is length, d is diameter, and $$I = \frac{\pi}{64}d^4.$$

Ball-Joints Preloading Spring

A preload spring may be used to preload the ball-joints of the struts. In a specific example, the preload force may be set to be 7N to handle forces at the instrument tip. Here, maximum forces by stall torque may be taken as a reference to keep the struts engaged, despite overloading. The preload spring may be placed almost parallel to the strut to minimize length perturbations during movement, since perturbations in spring length may indicate a variation in stored elastic energy. A change in stored elastic energy may impose a preferred position for the mechanism as it naturally searches for its minimum energy state. This searching for its minimum energy state may introduce parasitic forces on the actuators, which may be undesired.

Using a low stiffness spring instead of a high stiffness spring may help in minimizing this effect, as length variation for a lower stiffness has a smaller change in stored energy. However, a standard low stiffness steel spring typically has a lower eigenfrequency, which may be another source of disturbance. Additionally, a standard steel coil spring may be hard to clean. Accordingly, in some examples, a thermoplastic polyurethane (TPU) may be chosen as preload element. TPU is an elastomer, which is known for having large strain properties (sometimes 500%), excellent resistance to rupture, and good damping properties. Consequently, a large deformation of a relatively low stiffness TPU preload element may be used to obtain the required preload, while vibrations may be decreased by structural damping of the material. It will be appreciated, however, that the preloaded spring may also be of other materials, including the aforementioned steel if the aforementioned drawbacks are accepted.

Crank Shape

Figure 6:
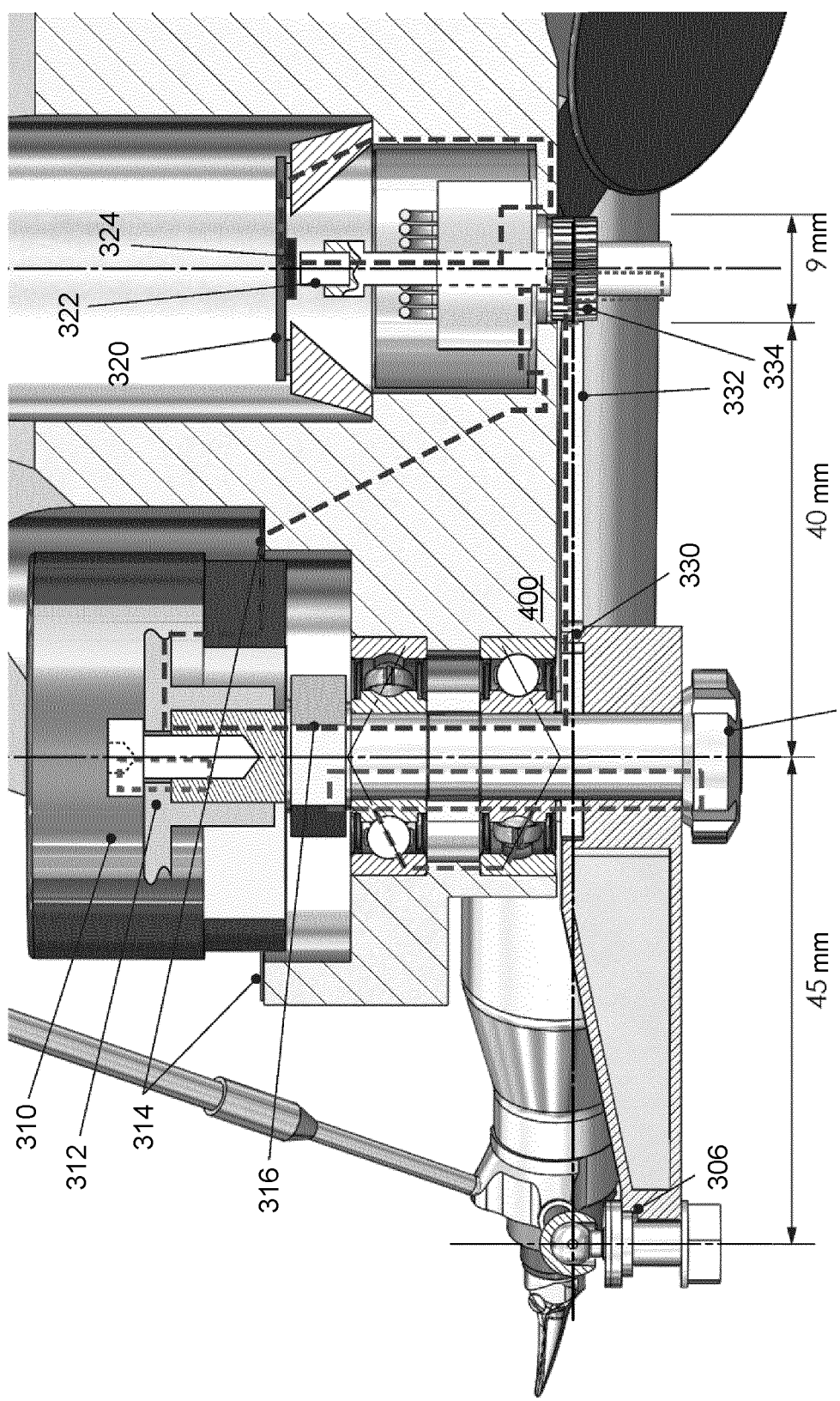
FIG. 6 shows a sectioned view of a crank, gear segment, support axis, bearings setup, encoders and motor for driving, measuring and supporting a strut.

FIG. 6 shows a sectioned view of a crank, gear segment, support axis, bearings setup, encoders and motor for driving, measuring and supporting a strut. In the specific example of FIG. 6, the crank is shown to have a length of 45 mm, while allowing a 900 rotation to make the required stroke. An impression of the crank shape can be obtained from FIGS. 5A, 5B and 6. The crank may be a closed box to cope with the load case and to minimize inertia. The load case may comprise bending and torsion, which may be introduced due to the ball-joint orientation. A box construction may enable most material to contribute to the stiffness of the load. The crank may be designed symmetrical to be usable at both sides of the manipulator to decrease cost.

Crank Drive

As seen in FIGS. 5 and 6, the crank may be driven by an electric motor, driving a gear segment 332 via an anti-backlash gear. A gear segment 332 may be chosen as it may be used as a counterweight balancing gravitational forces on the crank mechanism (see also FIG. 15 and the section 'weight compensation') while simultaneously providing a back-drivable transmission to the motor. For balancing purpose, the segment may be located opposite to the crank. Furthermore, a single step transmission may be chosen, as it may reduce friction, gear tooth irregularities and parts count, compared to using multiple step gear transmissions. A disadvantage, however, may be having less flexibility in obtaining an inertial match between the motor and the mechanism. A small gear module may be chosen, such that the transmission may be made compact. The motor may be customized, for example, with a second shaft output, which is convenient for attaching encoders. Given this or another type of motor, transfer ratios may be chosen such that forces exerted on the strut as well as the reaction force on the motor bearings are limited. Forces to the strut may be limited for patient safety, while forces at the motor may be limited to prevent motor bearing damage. Although choosing the motor pinion ≤10 mm makes $F_{pinion,stall} > F_{allowable\ radial\ force}$, the distance to the motor flange may be smaller (<2.5 mm), which may decrease the moment exerted on the motor bearings. Moreover, a smaller gear may enable the pinion to fit through a flange hole of the motor, which may be convenient for assembly and disassembly and which may allow for a permanent fixation of the motor pinion.

Crank Drive Encoders

As may be seen in FIG. 6, the crank position may be measured at the crank rotation axis 302, which may function as a shaft for the (main) encoder 310. In some examples, an optical integrated absolute encoder may be chosen as a measurement device to measure and control the position of the crank, since sufficient space may be available while high accuracy may be desired. In a specific example, an encoder may be chosen with a 22-bit or 23-bit measurement resolution. In addition to the main encoder 310, an auxiliary encoder 324 may be placed on the motor side to increase system redundancy. In case of an encoder failure, the system may thereby avoid unsafe situations. Furthermore, this redundant auxiliary encoder 324 may provide the possibility for identifying gear irregularities, which may be accounted for in control. In a specific example, the auxiliary encoder 324 may be a 14-bit on-axis absolute magnetic encoder placed on a PCB 320, which simultaneously contains electronics for the motor.

Spherical Wrist and Tubes Assembly

Figure 7:
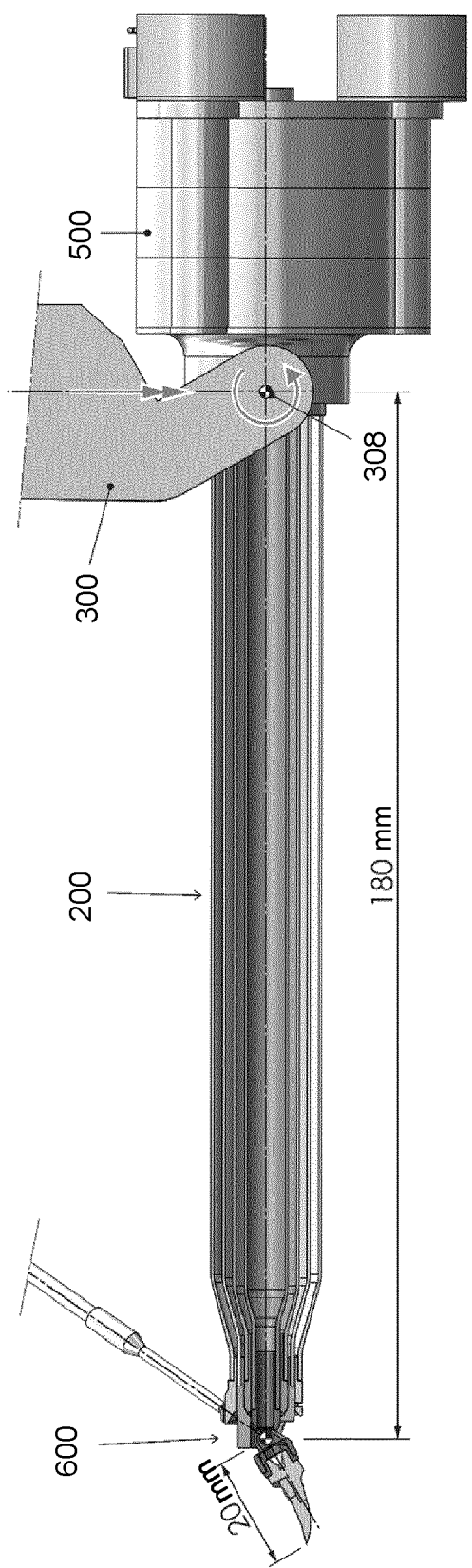
FIG. 7 shows a sectioned view of the spherical wrist and tube assembly while additionally showing the drive-box and drive-box crank.

FIG. 7 shows a sectioned view of the spherical wrist 600 and tube assembly 200 while additionally showing the drive-box 500 and drive-box crank 300. As can be seen in FIG. 7, the tube assembly 200 may be connected to the drive-box 500 which in turn may be connected to the drive-box crank 300 by a passive revolute joint. The drive-box crank 300 may additionally allow rotation around its own axis. To allow this rotation, a universal joint 308 may be provided in the center of the tubes. This universal joint 308 may facilitate the translation of the wrist 600 by the struts and cranks.

Spherical Wrist Layout

Figure 8:
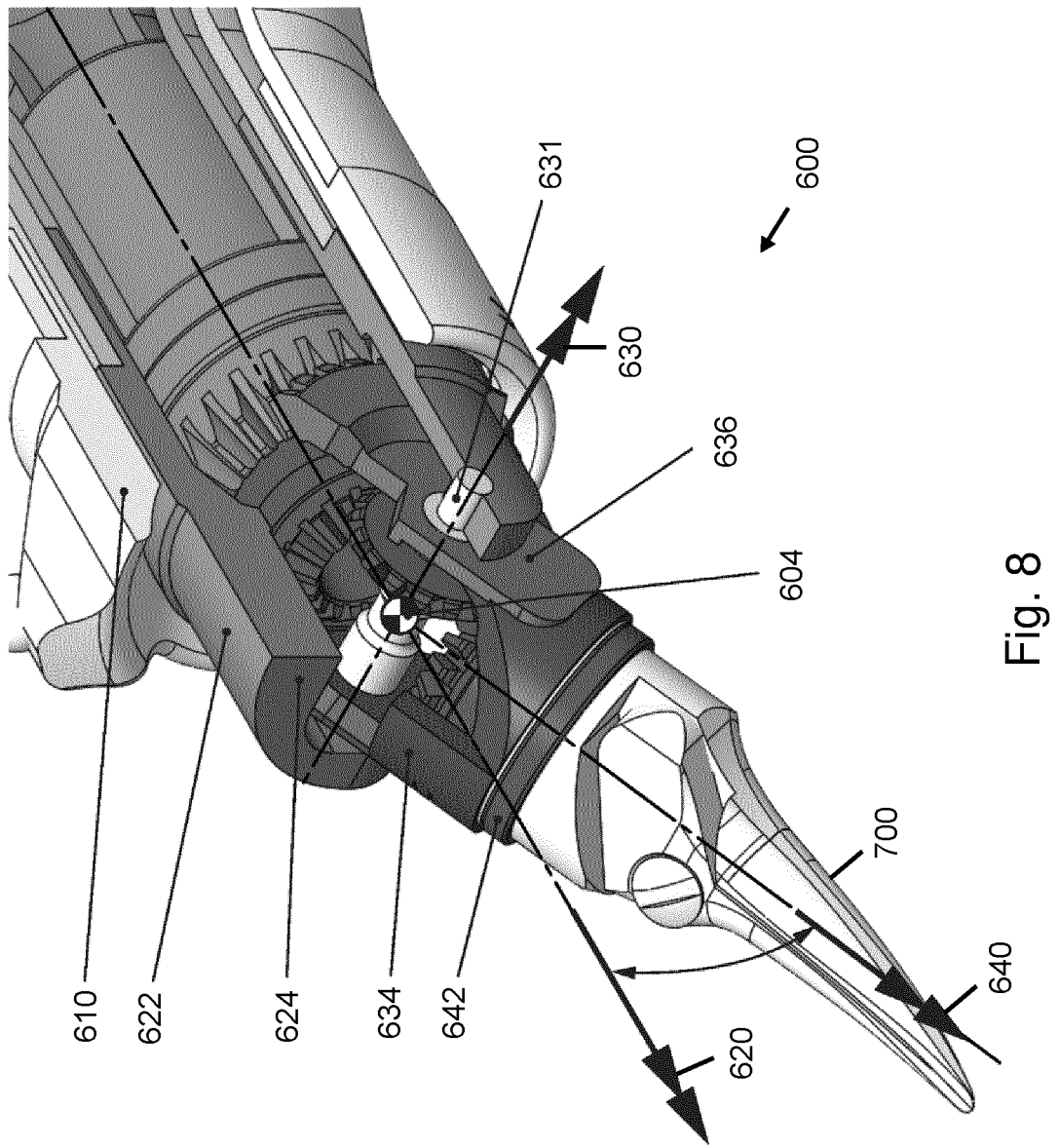
FIG. 8 shows a partly sectioned isometric view of the spherical wrist.

FIG. 8 shows a partly sectioned isometric view of the spherical wrist 600 holding the surgical instrument 700. The spherical wrist 600 may enable yaw 620, pitch 630 and roll 640 ($\theta_i$) of the instrument 700 as indicated in FIG. 8. The roll axis 641 may be placed last in the kinematic chain and may be aligned with the instrument axis such that the roll ($\theta_i$) can always be executed. The pitch 630 may determine the angle of the roll axis 641 with respect to the yaw axis 621, while the yaw axis 621 may provide the last rotational DOF. Roll 640 and pitch 630 rotations may be driven by bevel gears, while the yaw 620 may be driven directly by a tube. Although the wrist 600 is convenient from a mechanical point of view, from a control perspective, there may be a singularity if the roll-axis 641 and the yaw-axis 621 are aligned. The singularity may be avoided using control stops, for example, by limiting the pitch angle ≥2° or 3°. Such control stops may for example be implemented in software on a controller of the surgical robotic system. For example, a limitation of 2° in rotation may result in losing 0.18% of the total rotational range of motion, which may be regarded as neglectable. It is noted that an angle limitation is merely an example, and other control solutions may be used as well. In some examples, the rotational DOF may not be required to be controlled as accurately compared to translational DOF, as long as the instrument tip position is not compromised. Additionally, a mechanical stop 624 may be implemented for the point of singularity, which may function as a safety- and initialization feature.

Spherical Wrist Constraints

Figure 9:
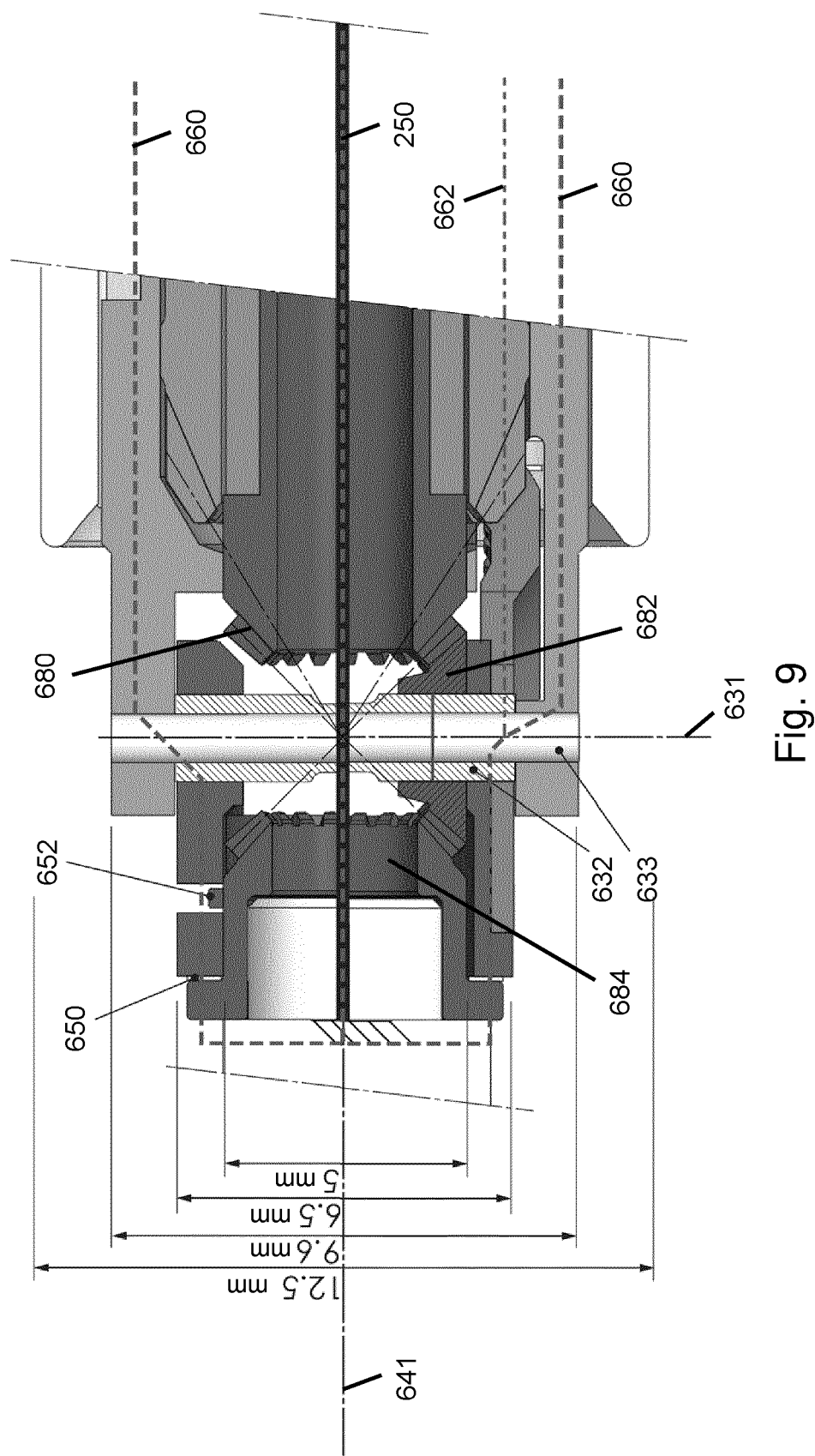
FIG. 9 shows a sectioned top-view of the spherical wrist.

FIG. 9 shows a sectioned top-view of the spherical wrist. Plain bearings may be deployed in the spherical wrist to constrain a guide DOF. Alternatively, rolling element bearings may result in lower friction; however, removal of non-sterile and patient-to-patient contaminants may be complicated for these bearings. However, friction in plain bearings may be reduced by using grease. A sterile and bio compatible grease may be obtained from various manufacturers. As can be seen in FIGS. 8 and 9, the roll axis 641 may be constrained in 5 DOF by a thrust-bearing 650 preloaded by a string 250 and a radial bearing preloaded by an elastic element 652. This bearing arrangement may be chosen over a double radial bearing arrangement as it may cause less friction, e.g., $T_{roll} \approx 6$ Nmm, and may result in a shorter instrument tip-to-wrist center distance. A shorter instrument may result in a smaller transfer ratio for pitch and yaw to the instrument tip. The pitch axis 631 and yaw part 622 together constrain the pitch part 634, which may contain the roll bearing arrangement. The pitch axis 631 may comprise an inner 633 and outer axis 632. The outer axis 632 may be clamped by the pitch part 634 and run over the inner axis 633. The inner axis 633 may be clamped by the yaw part 622 and constrain the pitch part 634 in the wrist. This bearing may also be preloaded as the force path 660 of the preload passes through these bearings.

Removal of the pitch axis may allow the wrist assembly to be disassembled for cleaning and sterilization. These pitch axis parts may be considered disposable and may be mass produced with suitable tolerances, e.g., by tube drawing companies.

The yaw part 622 may be constrained radially (2 DOF) by a plain bearing inside the outer tube part. The yaw tube may provide two plain bearings for the roll- and pitch gears tubes to constrain 2 radial DOF. As a result, the structural loop for the roll drive train may be stiffer with respect to a bearing between the roll and pitch tube. Furthermore, a less disturbed pitch tube may be convenient, since its rotational accuracy may be most sensitive to provide translational errors to the instrument tip. Additionally, from a manufacturing perspective, a single part providing bearings and axis may be also preferred, since a single part may allow for single fixation turning and or milling, which may enable high quality tolerances for bearings and the pitch axis to locate the bevel gear apexes; multiple bearing parts may require more well-defined and higher quality tolerated features. For example, each tube providing a bearing for a consequent tube requires at least two well defined and tolerated features. Longitudinal DOF for the yaw, pitch and roll tubes may be constrained at the drive-box to minimize additional friction in the wrist, despite tolerance disadvantages. However, a way of obtaining the desired tolerances is described under 'concentric tubes assembly'.

Spherical Wrist Preload Bearings

Figures 10A, 10B:
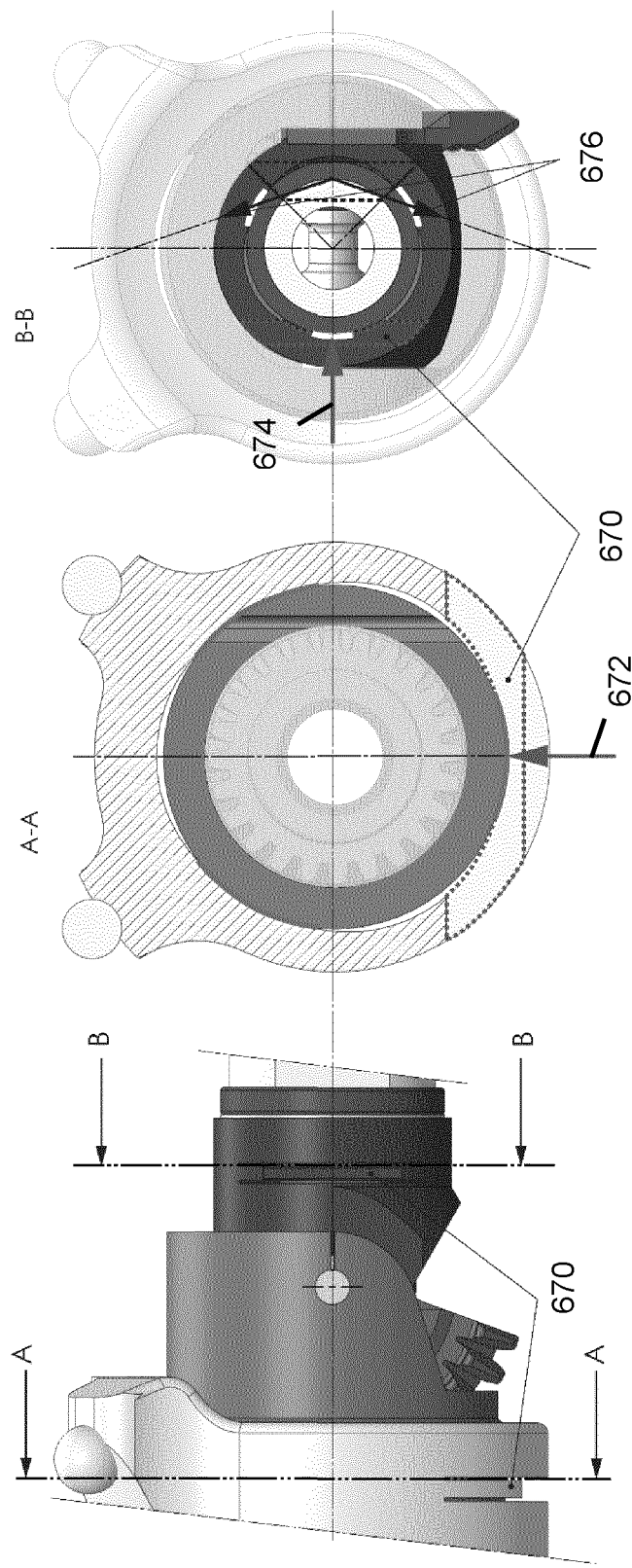

FIG. 10A shows a sideview of the yaw and roll plain bearing with preload elements 670, while FIG. 10B shows a sectioned view along planes A-A and B-B. The roll and yaw tube may have preload elements 670 to eliminate backlash in the radial direction of the tubes. FIGS. 10A and 10B includes two section views for illustrating the construction of the bearings. The bearing may provide three contact surfaces which may be spaced apart 120°. These surfaces may be made by reaming, which may provide a suitable tolerance fit. One of these contact surfaces may preload the yaw part, as it may be made into an elastic element by wire electrical discharge machining EDM. The preload element may receive an initial plastic deformation inward during manufacturing. As a result, an inserted axis may experience a preload 672 by elastically deforming the element outward. The remaining two bearing may face determine the shaft position, while they may be oriented towards the strut connection points to have a short structural loop. The roll plain bearing may be constructed similar to the yaw plain bearing. However, the orientation may be tuned to the bevel gear forces 676 to minimize the required preload 674. As can be seen in FIG. 10B, the gear forces in both directions may intersect the bearing contact surfaces. As a result, the gear forces may create no or little moment for rolling out of its bearing contacts.

Spherical Wrist Gears

FIG. 11A shows a sectioned side view of the spherical wrist at a pitch angle of 0 degrees, while FIG. 11B shows a sectioned side view of the spherical wrist at a pitch angle of 70 degrees. In both FIGURES, bevel gears are made transparent for visibility. Bevel gears may be used for driving roll and pitch as described in previous sections. In a specific example, a pressure angle α of 20° may be chosen for the bevel gears, while a gear module 0.3 may provide enough teeth (≥13) to avoid significant profile shift while teeth size may be still suitable for proper manufacturing and gear strength is sufficient. The gear module may be taken at the medium diameter of the gear ($d_m$).

As shown in FIGS. 11A and 11B, the pitch gears may pre-loaded by a preload string 250 running over the pitch axis, which may introduce a moment (see also FIG. 9). In a specific example, the pitch gear may be given a transfer ratio of 0.64 to provide space for the roll gear tube plain bearing in the yaw-part, which is described in previous sections. The transfer ratio may be convenient for the pitch gear accuracy to the instrument tip and may simplify the assembly as it decreases part count and stacking of tolerances. These components may be machined during a single fixture, which may ensure that features, such as gears and axis, are well defined with respect to each other. In a specific example, zirconia bevel gears may be chosen over stainless steel. Although both materials may have abundant performance to be applied as bevel gears, zirconia may be accompanied by a ceramic injection molding (CIM) process, which is advantageous for mass production. Moreover, zirconia may be treated such that it has a limited sticks-slip effect.

Concentric Tubes Assembly

Figure 12:
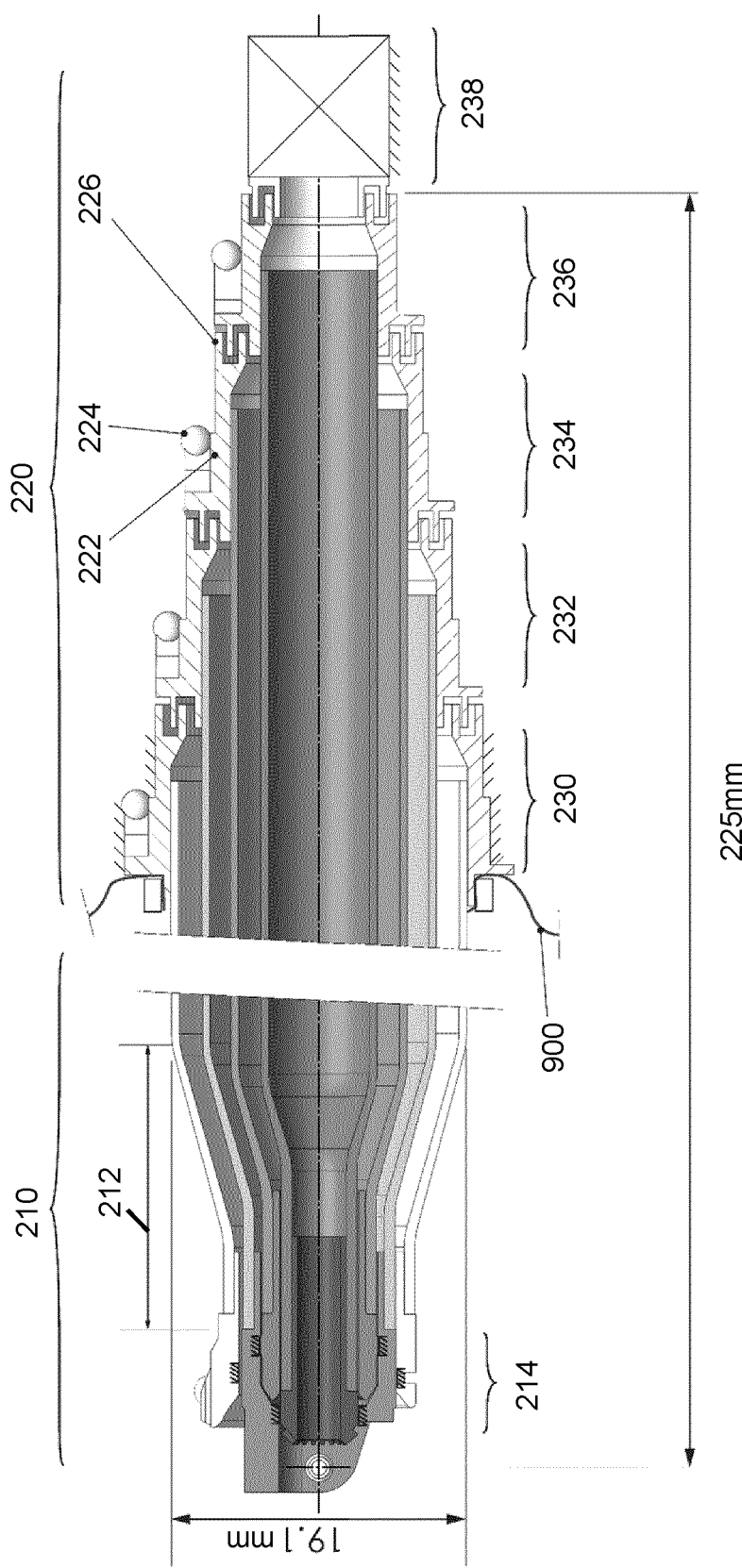
FIG. 12 shows a sectioned sideview of the tube assembly.

FIG. 12 shows a sectioned sideview of the tube assembly. Herein, concentric tubes may be used to transmit torque to the spherical wrist for driving roll, pitch and yaw. Such a design may provide one or more advantages, such as:

1. Convenient sterilization, since medical staff may be familiar with sterilization of tubular instrumentation, such as trocars and minimal invasive equipment.
2. Multiple DOF may be driven axisymmetric along the same centerline.
3. Unlimited (angular) displacement, as opposed to push and pull rods
4. Straightforward sealing due to the axis-symmetry
5. Straightforward (dis-)assembly, as tubes can use centering features.
6. Concentric fixation of tube end-parts, such as bevel gears As seen in FIG. 12, the tubes assembly may comprise four tubes 230-236, having parts fixated to each side of the tubes. These parts may constrain the tube or transmit forces. On the wrist side, the outer tube 230 may provide a connection for the struts, which may control the tube's assembly position. The wrist side constraints of the other tubes are described under the heading 'spherical wrist constraints'. The constrained DOF on the drive-box side may be as follows: outer tube 230: 6 DOF, yaw tube 232: 4 DOF, pitch tube 234: 4 DOF, roll tube 236: 4 DOF, end seal 238: 6 DOF.

The coupling parts may contain axial labyrinth seals for sealing between respective tubes. In the labyrinth, a sterile lipid/grease may be applied. The greased-filled axial labyrinth seals may create a sterile barrier to prevent non-sterile contamination by the drive-box during surgery. This may allow a coupling between sterile and non-sterile components, without contaminating the sterile zone, see also under the heading 'sterile barrier'. As can be seen in FIG. 12, the fixated parts on the wrist side may be pressed into the tubes and have an axial stop to define the fixated position. The tube's coupling position may be tuned with respect to the other parts to deal with manufacturing tolerances of the tubes and parts. In a specific example, fixation of all the parts may be established by glue. Additionally, this glue may be used to fill out gaps and cavities, which otherwise may be hard to clean and sterilize.

Swaging of Tubes

Tube swaging may enable larger diameter tubes to transmit torque to the wrist, instead of smaller straight tubes with a direct fit to the wrist. Swaging is a (cold) forming process for reducing a tube diameter, which may be applied locally. Therefore, a larger diameter tube may be locally swaged, see the swaged tube portion 212 in FIG. 12, to fit the components of the wrist. As a result, the stiffness of the tubes may be increased with respect to a design with straight tubes, since $k_{tube} \propto D^4$. Accordingly, the virtual backlash may be decreased by deploying the swaging technique.

Instrument and Actuation

Figure 13B:
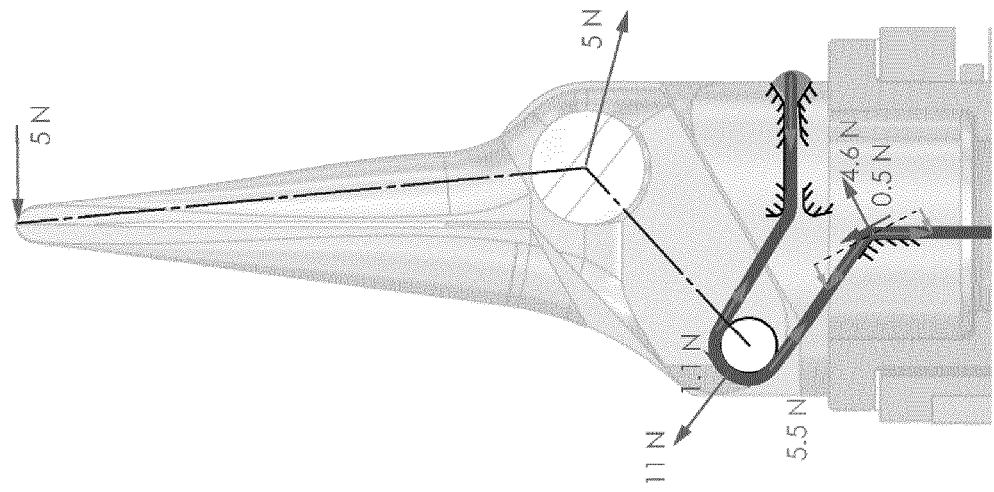
FIG. 13B shows a top-view of the needle holder instrument of FIG. 13A, showing forces evoked by applying a maximum permissible force to a Dyneema string.
Figure 13A:
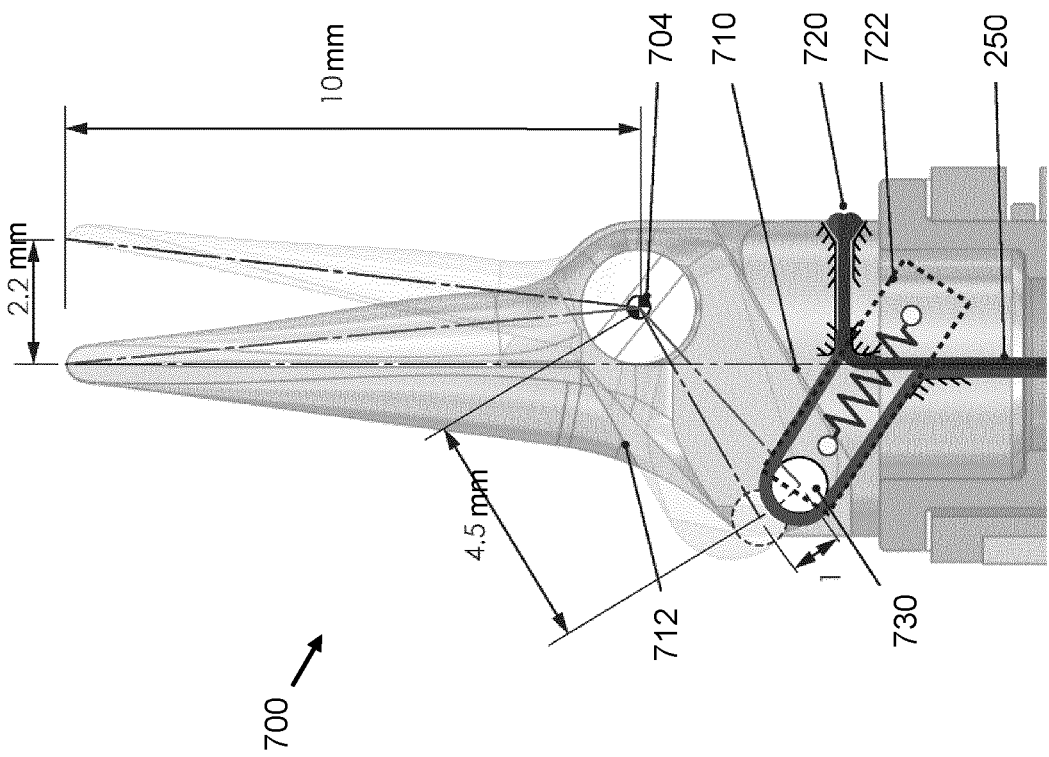
FIG. 13A shows a top-view of a needle holder instrument with a schematic illustration of its actuation principle and the fixation of the preload string.

FIG. 13A shows a top-view of a needle holder instrument 700 with a schematic illustration of its actuation principle and the fixation of the preload string. As also shown in this example, the instrument shape may be kept similar to conventional instrumentation. However, some adjustments may be made to provide actuation of the jaw. For example, compared to a conventional needle holder instrument, the instrument length of FIG. 13A may be shortened by ⅔, while the angular motion range may be increased to keep the opening width similar to ≈2.2 mm. (Much) further decreasing the instrument length may be less convenient for making suture knots.

An asymmetric design may be chosen over a symmetric design, as it may reduce components, provide a stationary reference point, and may provide more space for an actuation mechanism. As can be seen in FIG. 13A, the instrument may comprise two main parts; a stationary side and a clamping side, rotating around an asymmetrically placed hinge point 704 which may be provided by a tapered screw. The stationary side may function as a reference point for the instrument location, as it may be fixated to the roll axis. In other words, a surgeon may identify the actual point that is controlled. The jaws may be distinguished by the color marking of the jaws.

The instrument gripping force may in a specific example be ≈5N and may be provided by an ultra-high-molecular-weight polyethylene string 250 over a sliding pulley 730. The sliding pulley 730 may compensate for the lever ratio of the jaw to reduce the required actuation force. The gripping force may be limited by a mechanical stop 710 to prevent damaging the instrument tip in case of over-actuation. Another mechanical stop 712 may limit opening of the jaws, which may happen via a spring. This spring may keep the jaw 'normally open' and hold the string under tension. In a specific example, the pretension in the actuator string may obtain ≈0.2-0.6N of force for spring volume 722. This force may be enough to keep the string preloaded.

The preload string may for example be made out of ultra-high-molecular-weight polyethylene (UHMWPE) or high-modulus polyethylene (HMPE) fibers, for example out of so-called Dyneema fibers. The string may be fixated at either or both sides by turning over an end-part, thereby causing a thickening. Glue may be applied to keep the string formed at and near the thickened part, such that the thickened part is maintained during assembly of the string. The thickened part may fixate the string by hooking into a slot at the wrist, while the other end may be fixated and tensioned at the drive-box. For example, at the wrist, such fixating may comprise fixating the string to the center of a pulley at the string fixation point 720, while winding the string multiple revolutions around this pulley such that the string clamps itself onto the pulley. The fixation to the center of the pulley may prevent the complete winding from slipping over the pulley. Such fixation may for example be obtained as follows: firstly, the string may be wrapped several times into slots on the pulley. Secondly, a setscrew may clamp the string to the center of the pulley. Thirdly, the string may be wound-up a number of times over the pulley. Lastly, the string may be tensioned and held by a non-back drivable worm gear, similar to a guitar string. It will be appreciated that this way of fixation is merely an example, and that any other suitable fixation may be used as well.

FIG. 13B shows a top-view of the needle holder instrument of FIG. 13A, showing forces evoked by an example application of a Dyneema string, and in particular, by applying a maximum permissible force to the Dyneema string.

Preload and Instrument Actuation Mechanism

Figure 14:
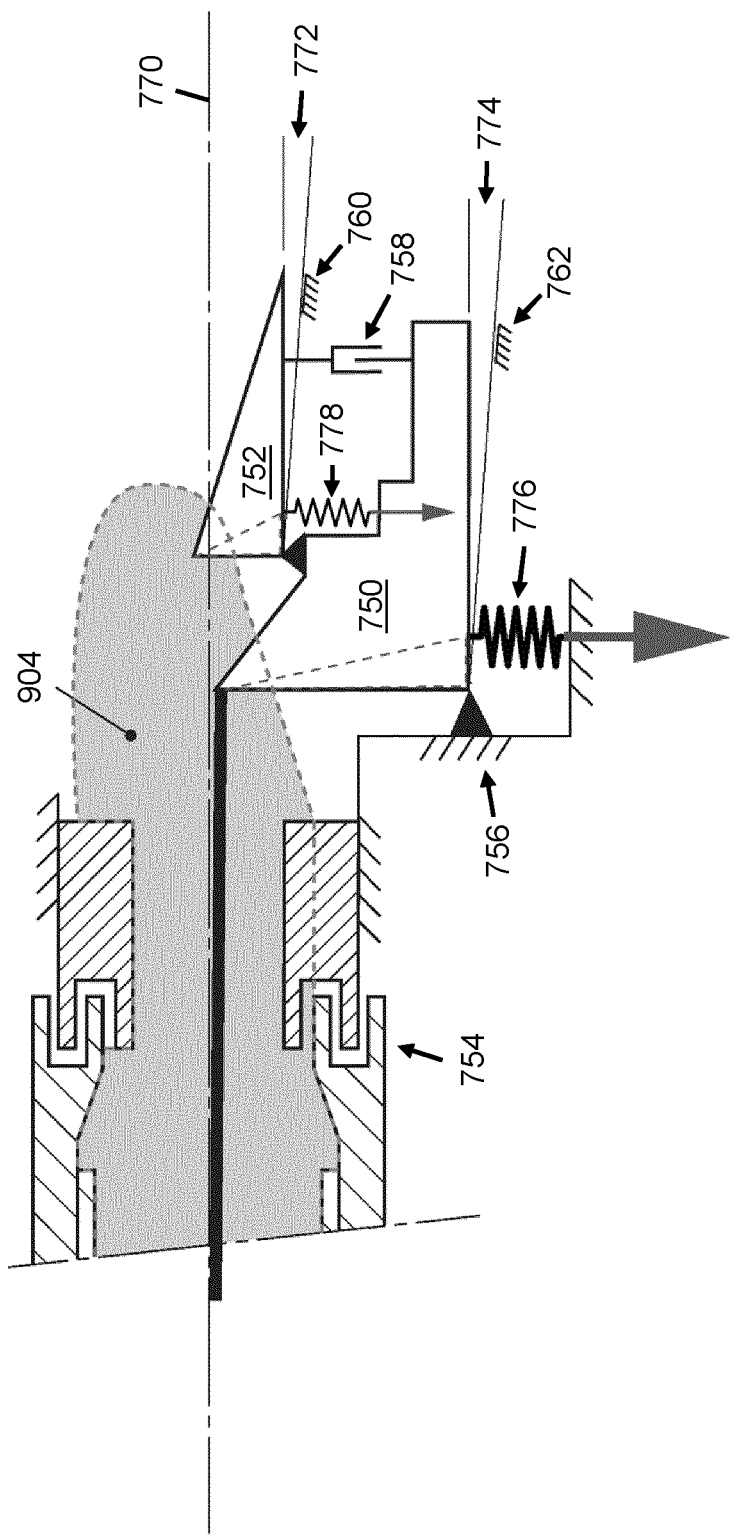
FIG. 14 shows a schematic of a preload and actuation mechanism.

FIG. 14 relates to a mechanism, which is shown schematically in FIG. 14, which may reduce preload variations to the wrist while providing actuation of the jaw and facilitating length variations. As a result, wrist friction may be decoupled from jaw actuation and wrist configuration, as friction is proportional to the preload felt by the wrist. The total preload force to the wrist may be provided by $c_{preload}$ 776. As a result, the jaw force may be controlled, which is convenient for manipulation of delicate tissue and which may enable haptic feedback. In case of no actuation, a spring ($c_{beak\ preload}$, 778) may tension the jaw string with a force, being in a specific example ≤0.2N, which may correspond to the micro spring preload for opening the jaw of the instrument. The preload provided to the strings may be desired to have little variation and to stay constant regardless position perturbations. Force variation may be reduced by decreasing spring stiffness. However, a small spring stiffness may require long tensioning stroke and may decrease the eigenfrequency. As a result, integration of the spring is more complicated, and natural vibration could act as a disturbance. Instead, a stiff spring may be reduced by a lever to provide a similar nearly constant preload. The application of the preload may be performed during setup of the surgical robotic system, while the sterile zone may be maintained. Prior to preload, both bodies 750, 752, referring to the jaws of the surgical instrument, may rest on a mechanical stop while the strings may be attached to the bodies. The strings may then be tensioned by a tensioning mechanism until the bodies are lifted-off their mechanical stops.

Weight Compensation

Figure 15:
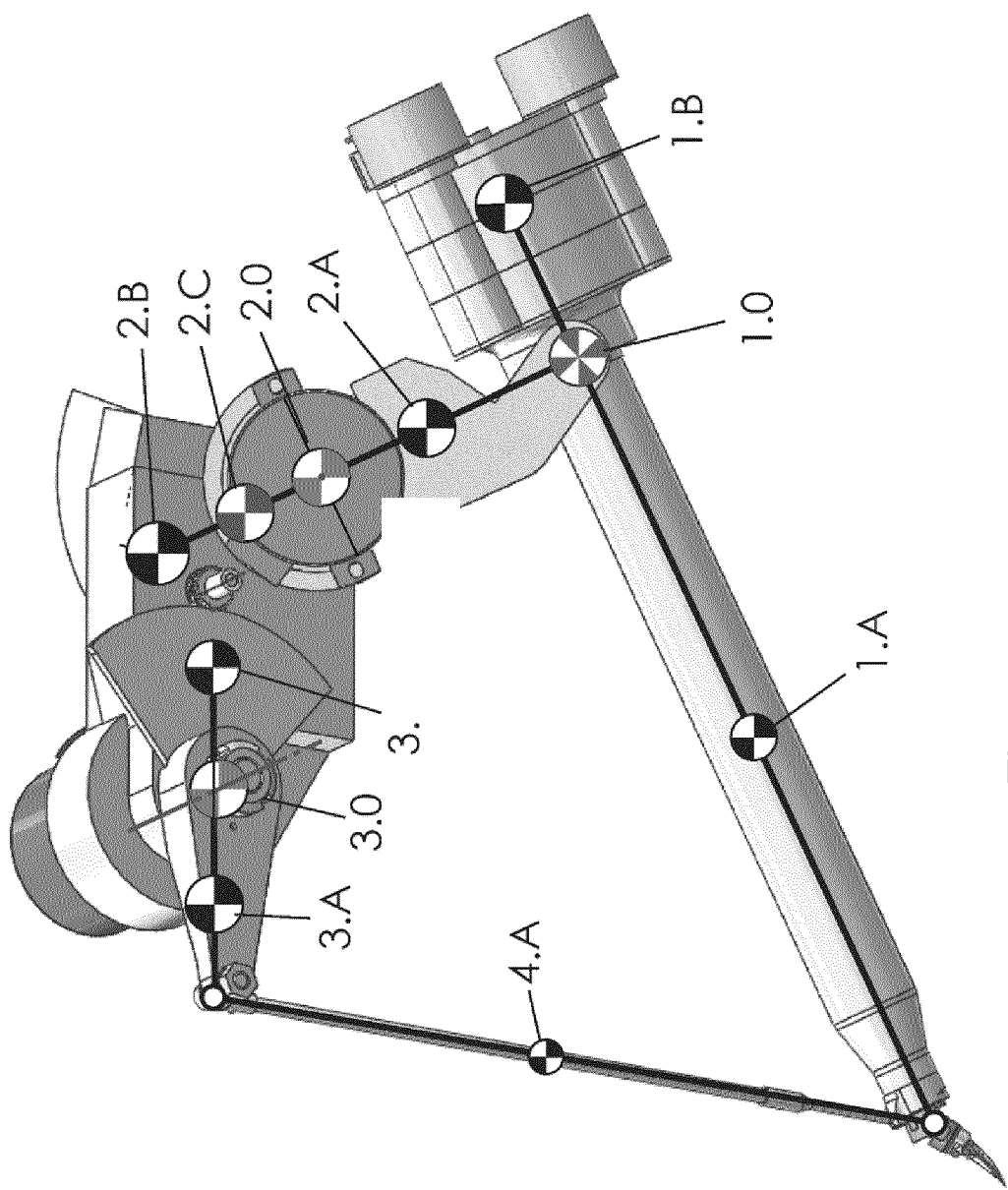
FIG. 15 shows a sideview of the manipulator, indicating the approximate location of center-of-mass for balancing the manipulator.

FIG. 15 shows a sideview of the manipulator of the surgical robotic system, indicating the approximate location of center-of-mass (COM) for balancing the manipulator. Weight compensation may be used to avoid motor power consumption by gravitational force and to avoid the manipulator collapsing onto a patient in the case of power down. The manipulator may be mass-moment balanced, whereby components of the manipulator may mutually balance each other without adding much additional mass. For example, the tube assembly and drive-box may function as each other's counter mass, as can be seen in FIG. 15 showing the center of mass 1.A of the tube assembly and wrist, the center of mass 1.B of the drive-box, and the combined center of mass 1.0 of 1.A and 1.B. In principle, configuration independent balancing may require the total center-of-mass of a certain chain of links to stay on the same location, regardless of configuration. For the manipulator, this location may be located at the rotation axis with respect to the fixed world, e.g., to the support structure as described with reference to FIG. 3. This type of balancing may compensate for both gravity in any orientation as well as reaction forces to the frame, since m·ẍ=0 and consequently m·z̈=F=0. Typically, one may choose to balance the most significant masses, as perfect balancing may require additional links which may complicate the design of the manipulator. A gyroscope may be added to the frame to measure the manipulator's orientation with respect to gravity, which may allow a feed forward algorithm in a control system to compensate for gravity by controlling motor(s).

FIG. 15 shows an example of mass-moment balancing, where COMs 1.A and 1.B balance each other such that the mutual COM is located at 1.0. This COM 1.0 and COM 2.A may be balanced by COM 2.B and tuned by a counterweight with COM 2.C into a common COM 2.0, which may be located at the rotation point of the link and which may be the rotation point with respect to the support structure. COM 3.A may be balanced by COM 3.B. COM 4.A may be chosen not to be balanced, since balancing may only compensate little force (e.g., 0.1N) while complicating the design.

In general, various other methods may be used for weight compensation. In general, the manipulator structure may be designed to have mass concentrated close to the intended COM, given inertia $J \propto r^2$, while balancing moment $M_{balance} \propto r$. It is further noted that the degree of motion compensation may be kept to a minimum or at least reduced by using a short instrument, in that a shorter instrument length may require less translation to compensate for the instrument rotations.

Sterile Barrier

Figure 16:
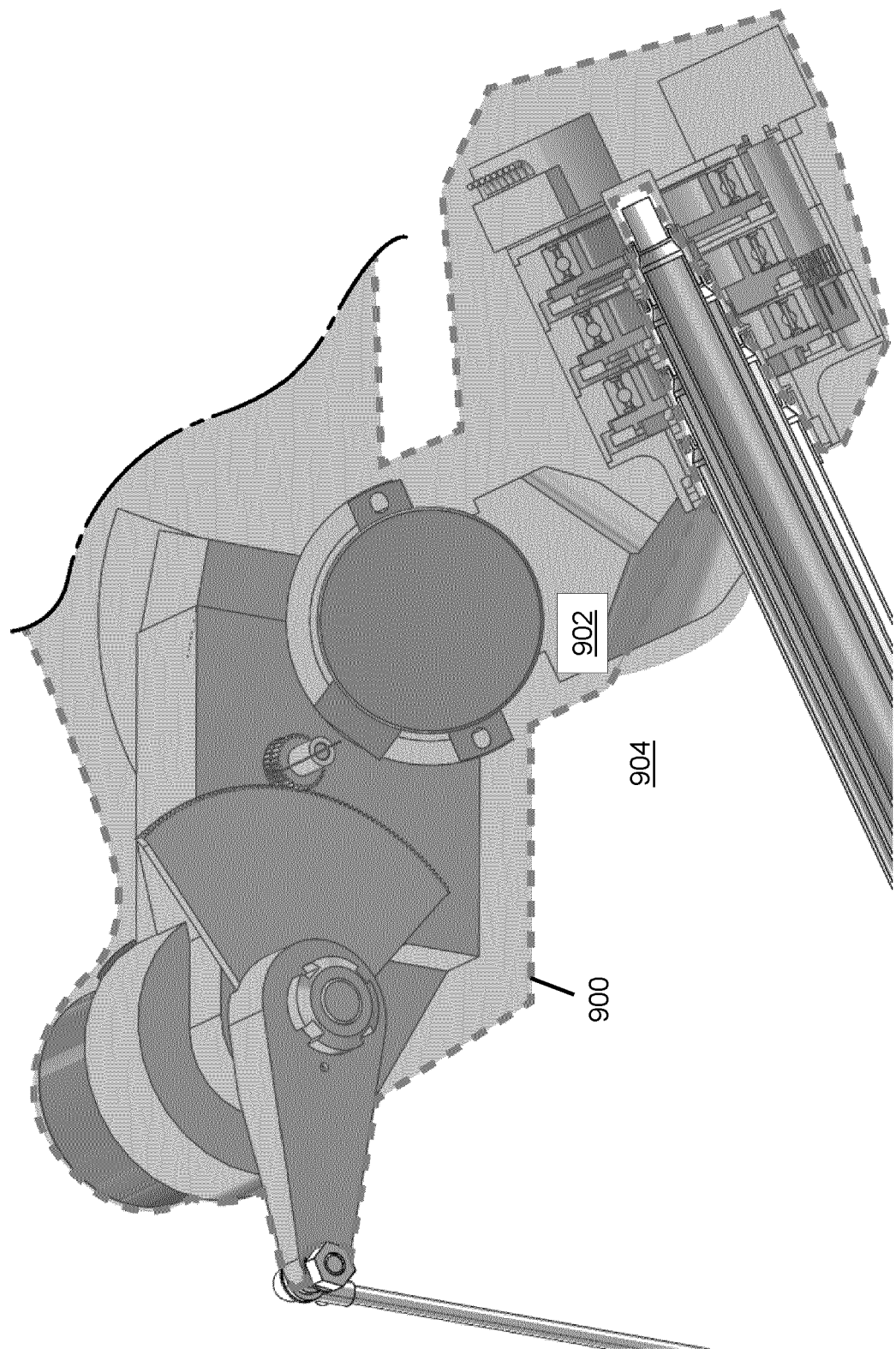
FIG. 16 shows a partly sectioned view of the surgical robotic system, showing a sterile barrier which is at least in part provided by a drape.

FIG. 16 shows a partly sectioned view of the surgical robotic system, showing a sterile barrier which is at least in part provided by a drape 900. In some examples, the sterile barrier may be provided by a combination of the drape 900 and sterile grease filled labyrinth seals as described elsewhere in this specification. In general, the sterile barrier may shield the surgical workspace and sterile manipulator components from non-sterilized manipulator components during surgery. Accordingly, a non-sterile but shielded zone 902 and a sterile zone 904 may be formed.

The design of the manipulator may facilitate sterilization. For example, the spherical wrist and tube assembly may each be sterilizable components which may be coupled to the drive-box 500 prior to surgery, and which may be designed for assembly and disassembly for such sterilization, similar to conventional surgical instrumentation. Additionally, the tube assembly may be designed to be coupled to the drive-box, while providing a sterile barrier to prevent non-sterile contamination by the drive-box.

In general, sterilization issues may be avoided if instrumentation enables easy cleaning. This may be achieved if the wrist can be disassembled, while individual parts of the wrist may be designed to avoid hard to reach geometrical cavities, such as blind holes. As previously described with reference to FIG. 9, the wrist may be disassemble-able for cleaning and sterilization, for example by the pitch axis of the wrist being removable. The respective pitch axis parts may be considered disposable and may be mass produced with suitable tolerances, e.g., by tube drawing companies.

A mechanical connection run between sterile and non-sterile components to transmit forces and torques to the instrument, which may be designed to avoid contamination of the sterile zone. The connection of the struts to the base structure, e.g., the frame, may be made by running the drape in between the fixation feature to the crank. The connection of tubes may be done inside the shielded zone, which may in principle contaminate the couplings of the tubes. However, the sterile zone inside the tube assembly may be maintained by axial labyrinth seals, while the drape may be attached to the tube assembly, as also previously illustrated in FIG. 12.

Assembly of the sterile components may be done prior to surgery. As a first step, the drape 900 may be attached to the tube assembly, which may then be coupled to the drive-box. Thereafter, the drape 900 may be positioned and fixated around the manipulator. Positioning of the drape 900 may be done according to markings on the drape, which may help with aligning the drape to the manipulator. The drape may be fixated by sterile rubber bands and tape to minimize the volume taken by the drape so as to maintain a clear view of the surgical workspace. Some drape surface may not be fixated to facilitate movement of the cranks. The corresponding excess drape surface may be limited to allow local flexing and folding at drape positions close to the crank's rotation axis. The fixation points of the drape may be part of the frame and associated frame panels (not shown in any Figures). Such frame panels of the frame may function as a form of shielding for protecting the drape from the gears and vice versa.

It should be noted that the above-mentioned embodiments illustrate rather than limit the invention, and that those skilled in the art will be able to design many alternative embodiments without departing from the scope of the disclosure described herein.

Any reference signs placed between parentheses shall not be construed as limiting. Use of the verb "comprise" and its conjugations does not exclude the presence of elements or stages other than those stated. The article "a" or "an" preceding an element does not exclude the presence of a plurality of such elements. Expressions such as "at least one of" when preceding a list or group of elements represent a selection of all or of any subset of elements from the list or group. For example, the expression, "at least one of A, B, and C" should be understood as including only A, only B, only C, both A and B, both A and C, both B and C, or all of A, B, and C. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

LIST OF REFERENCE AND ABBREVIATIONS

The following list of references and abbreviations is provided for facilitating the interpretation of the drawings and shall not be construed as limiting the claims.

1.A center of mass of tube assembly and wrist
1.B center of mass of drive-box combined center of mass of 1.A and 1.B
2.A center of mass of drive-box crank
2.B center of mass of gear segment
2.C center of mass of added counterweight
2.0 combined center of mass of 2.A, 2.B and 2.C
3.A center of mass of crank
3.B center of mass of gear segment
3.0 combined center of mass of 3.A and 3.B
4.A center of mass of strut
100 manipulator of surgical robotic system
150 strut
200 tube assembly as strut
202 tube assembly neutral axis
204 angle
210 spherical joint side
212 swaged tube portion
214 radial support (2 DOF)
220 drive-box side
222 coupling part to rotor
224 spheres
226 axial slat seal
230 outer tube, fixated (6 DOF)
232 yaw tube (4 DOF)

234 pitch tube (4 DOF)
236 roll tube (4 DOF)
238 end seal, fixated (6 DOF)
250 preload string
300 crank
302 crank rotation axis
304 ball-joint
306 centering hole for ball-joint alignment
308 universal joint
310 main encoder
312 encoder shaft connection
314 leaf spring
316 measurement loop
318 locking nut
320 printed circuit board
322 magnet
324 auxiliary encoder
330 alignment pin
332 gear segment
334 preload gear
400 frame
402 rotational axis of support structure
500 drive-box
600 spherical wrist
602 ball-joint
604 wrist center of rotation
606 arm
610 fixed part
620 yaw
621 yaw axis
622 yaw part
624 mechanical stop
630 pitch
631 pitch axis
632 outer pitch axis
633 inner pitch axis
634 pitch part
636 pitch gear segment
640 roll
641 roll axis
642 roll part
650 trust bearing
652 elastic element
660 force path
662 torque path
670 preload elements
672 preload force
676 bevel gear force
680 yaw bevel gear
682 pitch bevel gear
684 roll bevel gear
700 instrument
702 instrument length
704 hinge point
710 mechanical stop 1
712 mechanical stop 2
720 string fixation point
722 spring volume
730 sliding pulley
750 body 1
752 body 2
754 roll tube+labyrinth seal
756 drivebox
758 jaw actuator
760, 762 stop
770 centerline
772, 774 clearance
776 Cpreload
778 Cjaw preload
800 microscope
802 distance to patient
804 field of view
806 workspace
808 desired range of translation
900 drape
902 shielded zone
904 sterile zone

The invention claimed is:

1. A surgical robotic system, comprising:
a spherical wrist comprising a surgical instrument, wherein the spherical wrist comprises a yaw axis, a pitch axis and a roll axis to provide the surgical instrument with three rotational degrees of freedom, the three rotational degrees of freedom including a roll rotation about a longitudinal axis of the surgical instrument;
an elongated shaft, wherein the spherical wrist is attached to a distal end of the elongated shaft, wherein a drive assembly is attached to a proximate end of the elongated shaft, wherein the elongated shaft is configured to transmit actuation forces from the drive assembly to the spherical wrist to actuate rotation of the spherical wrist, and wherein the elongated shaft is a tube assembly comprising a concentric arrangement of at least three tubes, wherein each respective tube is configured to transmit a respective actuation force from the drive assembly to the spherical wrist to affect a rotation about a respective axis;
wherein the surgical instrument is a hinged surgical instrument comprising jaws, wherein the jaws are biased in a normally open position by a resilient biasing element, wherein the surgical instrument is actuatable by the drive assembly towards a closed position by a string which runs from the drive assembly through the elongated shaft and the spherical wrist to the surgical instrument, and wherein the string is preloaded to preload the surgical instrument and the spherical wrist, and wherein said preloading of the string applies an axial tension on the tube assembly, wherein the spherical wrist is actuatable by the tube assembly to rotate about the roll axis via a roll bevel gear and about the pitch axis via a pitch bevel gear, wherein the string runs over a pitch bevel gear shaft so as to apply a lateral force on said shaft to preload the pitch bevel gear onto a yaw bevel gear and the roll bevel gear.

2. The surgical robotic system according to claim 1, wherein the string is elastically attached to or in the surgical instrument via a resilient fixation element.

3. The surgical robotic system according to claim 2, wherein the resilient fixation element is a pulley, and wherein the string is attached to the pulley by being wound multiple revolutions around the pulley.

4. The surgical robotic system according to claim 1, wherein the string comprises or is made out of ultra-high-molecular-weight polyethylene, UHMWPE, or high-modulus polyethylene, HMPE, fibers.

5. The surgical robotic system according to claim 1, wherein the spherical wrist is directly actuatable by the tube assembly to rotate about the yaw axis via a respective tube of the tube assembly.

6. The surgical robotic system according to claim 1, wherein the yaw axis, the pitch axis and the roll axis of the spherical wrist form a serial kinematic chain, wherein the spherical wrist is rotated about the roll axis without influencing the yaw axis and the pitch axis.

7. The surgical robotic system according to claim 1, wherein the at least three tubes of the tube assembly are swaged at the distal end of the tube assembly.

8. The surgical robotic system according to claim 1, wherein the tube assembly is coupled to the drive assembly and/or to the spherical wrist with a respective coupling part, wherein the respective coupling part comprises a lipid- or greased-filled axial labyrinth seal for sealing between the respective tubes.

9. The surgical robotic system according to claim 1, wherein the hinged surgical instrument comprises a stationary jaw and a clamping jaw, wherein the clamping jaw is actuatable by the string.

10. The surgical robotic system according to claim 9, wherein the roll axis of the spherical wrist is aligned with a longitudinal axis of the stationary jaw of the surgical instrument.

11. The surgical robotic system according to claim 1, wherein the surgical instrument comprises a sliding pulley, and wherein the string runs over the sliding pulley to reduce a friction influencing the respective actuation force of the surgical instrument.

12. The surgical robotic system according to claim 1, wherein the surgical instrument comprises at least one of:
 a mechanical stop to avoid over-actuation of the surgical instrument, and
 a mechanical stop to limit opening of the jaws.

* * * * *